(12) United States Patent
Moberg et al.

(10) Patent No.: US 7,704,229 B2
(45) Date of Patent: Apr. 27, 2010

(54) INSERTION DEVICE

(75) Inventors: Sheldon B Moberg, Thousand Oaks, CA (US); Susie E. Maule, Pasadena, CA (US); Mark D. Holt, Moorpark, CA (US); Paul S. Cheney, II, Winnetka, CA (US); Arin N. Holecek, Lakewood, CA (US); Christopher G. Griffin, Sylmar, CA (US); Julian D. Kavazov, Arcadia, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 1485 days.

(21) Appl. No.: 11/050,101

(22) Filed: Feb. 3, 2005

(65) Prior Publication Data

US 2006/0173410 A1    Aug. 3, 2006

(51) Int. Cl.
  *A61M 5/00* (2006.01)
(52) U.S. Cl. .................................................... 604/110
(58) Field of Classification Search ................. 604/192, 604/198, 263, 110, 181, 187, 272, 93.01, 604/264, 268, 523, 288–89
See application file for complete search history.

(56) References Cited

U.S. PATENT DOCUMENTS

| 4,433,072 A | 2/1984  | Pusineri et al. |
| 4,494,950 A | 1/1985  | Fischell |
| 4,562,751 A | 1/1986  | Nason et al. |
| 4,671,288 A | 6/1987  | Gough |
| 4,678,408 A | 7/1987  | Nason et al. |
| 4,685,903 A | 8/1987  | Cable et al. |
| 4,723,947 A | 2/1988  | Konopka |
| 4,731,726 A | 3/1988  | Allen, III |
| 4,755,173 A | 7/1988  | Konopka et al. |
| 4,781,798 A | 11/1988 | Gough |
| 4,871,351 A | 10/1989 | Feingold |
| 5,080,653 A | 1/1992  | Voss et al. |
| 5,097,122 A | 3/1992  | Colman et al. |
| 5,101,814 A | 4/1992  | Palti |
| 5,108,819 A | 4/1992  | Heller et al. |

(Continued)

FOREIGN PATENT DOCUMENTS

EP    1 201 261 A2    2/2002

(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.

(Continued)

*Primary Examiner*—Manuel A Mendez
(74) *Attorney, Agent, or Firm*—Pillsbury Winthrop Shaw Pittman LLP

(57) ABSTRACT

An insertion device, generally used with an infusion set, including a needle being adapted for puncturing at one end and including at the opposite end a hub. The hub includes a handle part and a guard part that are capable of securing the needle through the use of locks. Locking structures are used to secure the insertion device in a position where the needle is covered in a locked position, avoiding unintended contact with the needle.

10 Claims, 23 Drawing Sheets

U.S. PATENT DOCUMENTS

| | | |
|---|---|---|
| 5,165,407 A | 11/1992 | Wilson et al. |
| 5,257,980 A | 11/1993 | Van Antwerp et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,320,725 A | 6/1994 | Gregg et al. |
| 5,322,063 A | 6/1994 | Allen et al. |
| 5,356,786 A | 10/1994 | Heller et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,497,772 A | 3/1996 | Schulman et al. |
| 5,522,803 A | 6/1996 | Teissen-Simony |
| 5,543,326 A | 8/1996 | Heller et al. |
| 5,545,143 A | 8/1996 | Fischell |
| 5,545,152 A | 8/1996 | Funderburk et al. |
| 5,569,186 A | 10/1996 | Lord et al. |
| 5,584,813 A | 12/1996 | Livingston et al. |
| 5,586,553 A | 12/1996 | Halili et al. |
| 5,593,852 A | 1/1997 | Heller et al. |
| 5,660,163 A | 8/1997 | Schulman et al. |
| 5,665,065 A | 9/1997 | Colman et al. |
| 5,665,222 A | 9/1997 | Heller et al. |
| 5,672,160 A * | 9/1997 | Osterlind et al. ............ 604/263 |
| 5,750,926 A | 5/1998 | Schulman et al. |
| 5,779,665 A | 7/1998 | Mastrototaro et al. |
| 5,791,344 A | 8/1998 | Schulman et al. |
| 5,904,708 A | 5/1999 | Goedeke |
| 5,917,346 A | 6/1999 | Gord et al. |
| 5,954,643 A | 9/1999 | Van Antwerp et al. |
| 5,965,380 A | 10/1999 | Heller et al. |
| 5,968,011 A | 10/1999 | Larsen et al. |
| 5,972,199 A | 10/1999 | Heller et al. |
| 5,999,848 A | 12/1999 | Gord et al. |
| 5,999,849 A | 12/1999 | Gord et al. |
| 6,017,328 A | 1/2000 | Fischell et al. |
| 6,043,437 A | 3/2000 | Schulman et al. |
| 6,056,718 A | 5/2000 | Funderburk et al. |
| 6,074,371 A | 6/2000 | Fischell |
| 6,081,736 A | 6/2000 | Colvin et al. |
| 6,083,710 A | 7/2000 | Heller et al. |
| 6,086,575 A | 7/2000 | Mejslov |
| 6,088,608 A | 7/2000 | Schulman et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,123,690 A | 9/2000 | Mejslov |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,259,937 B1 | 7/2001 | Schulman et al. |
| 6,302,866 B1 | 10/2001 | Marggi |
| 6,329,161 B1 | 12/2001 | Heller et al. |
| 6,355,021 B1 | 3/2002 | Nielsen et al. |
| 6,472,122 B1 | 10/2002 | Schulman et al. |
| 6,484,046 B1 | 11/2002 | Say et al. |
| 6,488,663 B1 | 12/2002 | Steg |
| 6,503,381 B1 | 1/2003 | Gotoh et al. |
| 6,514,718 B2 | 2/2003 | Heller et al. |
| 6,554,798 B1 | 4/2003 | Mann et al. |
| 6,558,320 B1 | 5/2003 | Causey, III et al. |
| 6,560,471 B1 | 5/2003 | Heller et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,685,674 B2 | 2/2004 | Douglas et al. |
| 6,689,265 B2 | 2/2004 | Heller et al. |
| 6,733,471 B1 | 5/2004 | Ericson et al. |
| 6,736,797 B1 | 5/2004 | Larsen et al. |
| 6,746,582 B2 | 6/2004 | Heller et al. |
| 6,749,740 B2 | 6/2004 | Liamos et al. |
| 6,809,653 B1 | 10/2004 | Mann et al. |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,894 B2 | 8/2005 | Mao et al. |
| 6,942,518 B2 | 9/2005 | Liamos et al. |
| 2002/0082665 A1 | 6/2002 | Haller et al. |
| 2002/0161288 A1 | 10/2002 | Shin et al. |
| 2003/0060781 A1 | 3/2003 | Mogensen et al. |
| 2003/0078560 A1 | 4/2003 | Miller et al. |
| 2003/0088166 A1 | 5/2003 | Say et al. |
| 2003/0152823 A1 | 8/2003 | Heller et al. |
| 2003/0168338 A1 | 9/2003 | Liamos et al. |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0220552 A1 | 11/2003 | Reghabi et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0074785 A1 | 4/2004 | Holker et al. |
| 2004/0093167 A1 | 5/2004 | Braig et al. |
| 2004/0111017 A1 | 6/2004 | Say et al. |
| 2005/0214585 A1 | 9/2005 | Bernatz et al. |

FOREIGN PATENT DOCUMENTS

| | | |
|---|---|---|
| EP | 1201261 A | 5/2002 |
| EP | 1338295 | 8/2003 |
| JP | 10-201852 | 4/1998 |
| JP | 10201852 A | 8/1998 |
| WO | WO 96/37246 A1 | 11/1996 |
| WO | WO 02/058537 A2 | 8/2002 |

OTHER PUBLICATIONS

Abel et al., "A Method for Evaluating in vivo the Functional Characteristics of Glucose Sensors," Biosensors, 1986, pp. 211-220, vol. 2.

Boguslavsky et al., "Applications of redox polymers in biosensors," Solid State Ionics, 1993, pp. 189-197, vol. 60.

Geise et al., "Electropolymerized 1,3-diaminobenzene for the construction of a 1-1'-dimethylferrocene mediated glucose biosensor," Analytica Chim. Acta.,1993, pp. 467-473, v18.

Gernet et al., "A planar glucose enzyme electrode," Sensors and Actuators, 1989, pp. 537-540, vol. 17, Elsevier Sequoia, Netherlands.

Gernet et al., "Fabrication and Characterization of a Planar Electrochemical Cell and Its Applications as a Glucose Sensor," Sensors and Actuators, 1989, pp. 49-70, vol. 18.

Gorton et al., "Amperometric glucose senosrs based on immobilized glucose-oxidizing enzymes and chemically modified electrodes," Analytica Chim Acta., 1991, pp. 43-54, v. 249.

Gorton et al., "Amperometric biosensors based on an apparent direct electron transfer between electrodes and immobilized peroxidases," Analyst, 1992, pp. 1235-1241, vol. 117.

Gough et al., "Two-Dimensional Enzyme Electrode Sensor for Glucose," Analytical Chemistry, 1985, pp. 2351-2357, vol. 57.

Gregg et al., "Redox polymer films containing enzymes," J. Phys. Chem., 1991, pp. 5970-5975.

Gregg et al., "Cross-Linked Redox Gels Containing Glucose Oxidase for Amperometric Biosensor Applications," Anal. Chem., 1990, pp. 258-263, vol. 62.

Heller et al., "Electrical Wiring of Redox Enzymes," Accounts of Chemical Research, 1990, pp. 128-134, vol. 23, No. 5.

Johnson et al., "In vivo evaluation of an electroenzymatic glucose sensor implanted in subcutaneous tissue," Biosensors & Bioelectronics, 1992, pp. 709-714, vol. 7.

Jonsson et al., "An Electrochemical Sensor for Hydrogen Peroxide Based on Peroxidase Adsorbed on a Spectrographic Graphite Electrode," Electroanalysts, 1989, pp. 465-468, v.1.

Kanapieniene et al., "Miniature glucose biosensor with extended linearity," Sensors and Actuators, 1992, pp. 37-40, vol. B, No. 10.

Kawamori et al., "Perfect Normalization of Excessive Glucagon Responses to Intravenous Arginine in Human Diabetes Mellitus With . . . ," Diabetes, 1980, pp. 762-765, vol. 29.

Kimura et al., "An immobilized Enzyme Membrane Fabrication Method using an Ink Jet Nozzle," Biosensors, 1988, pp. 41-52, vol. 4.

Koudelka et al., "In-vivio Behaviour of Hypodermically Implanted Microfabricated Glucose Sensors," Biosensors & Bioelectronics, 1991, pp. 31-36, vol. 6.

Mastrototaro et al., "An electroenzymatic glucose sensor fabricated on a flexible substrate," Sensors and Actuators, 1991, pp. 139-144, vol. 5.

Mastrototaro et al., "An Electroenzymatic Sensor Capable of 72 Hour Continuous Monitoring of Subcutaneous Glucose," 14th Int'l Diabetes Federation Congress, 1991.

McKean et al., "A Telemetry-Instrumentation System for Chronically Implanted Glucose and Oxygen Sensors," IEEE Transactions on Biomedical Eng., 1988, pp. 526-532, vol. 35, No. 7.

Monroe, "Novel implantable glucose sensors," ACL, 1989, pp. 8-16.

Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n.2.

Nakamado et al., "A Lift-Off Method for Patterning Enzyme-Immobilized Membranes in Multi-Biosensors," Sensors and Actuators, 1988, pp. 165-172, vol. 13.

Nishida et al., "Clinical applications of the wearable artificial endocrine pancreas with the newly designed . . . ," Path. and Treat. of NIDDM . . . , 1994, p. 353-358, No. 1057.

Shichiri et al., "An artificial endocrine pancrease—problems awaiting solutions for long term clinical applications of . . . ," Frontiers Med. Biol. Eng., 1991, pp. 283-292, v.3.

Shichiri et al., "Wearable Artificial Endocrine Pancreas with Needle-Type Glucose Sensor," The Lancet, 1982, pp. 1129-1131, vol. 2 (8308).

Shichiri et al., "Telemetry Glucose Monitoring Device with Needle-Type Glucose Sensor," Diabetes Care, May-Jun. 1986, pp. 298-301, vol. 9, No. 3.

Shichiri et al., "Normalization of the Paradoxic Secretion of Glucagen in Diabetics Who Were Controlled by the Artificial Beta Cell," Diabetes, 1979, pp. 272-275, vol. 28.

Shichiri et al., "Closed-Loop Glycemic Control with a Wearable Artificial Endocrine Pancreas," Diabetes, 1984, pp. 1200-1202, vol. 33.

Shichiri et al., "In Vivo Characteristics of Needle-Type Glucose Sensor," Hormone and Metabolic Research, 1988, pp. 17-20, vol. 20.

Shichiri et al., "A Needle-Type Glucose Sensor," Life Support Systems: The Journal of the European Society for Artificial Organs, 1984, pp. 7-9, vol. 2, supplement 1.

Shichiri et al., "The Wearable Artificial Endocrine Pancreas with a Needle-Type Glucose Sensor," Acta Pediatr, Jpn, 1984, pp. 358-370, vol. 26.

Shichiri et al., "Glycaemic Control in Pancreatectomized Dogs with a Wearable Artificial Endocrine Pancreas," Diabetologica, 1983, pp. 179-184, vol. 24.

Shichiri et al., "Membrane design for extending the long-life of an implantable glucose sensor," Diab. Nutr. Metab., 1989, pp. 309-313, vol. 2.

Shinkai et al., "Molecular Recognition of Mono- and Di-Saccharides by Phenylboronic Acids in Solvent Extraction and as a Monolayer," J. Chem. Soc., 1991, pp. 1039-1041.

Tamiya et al., "Micro Glucose Sensors Using Electron Mediators Immobilized on a Polypyrrole-Modified Electrode," Sensors and Actuators, 1989, pp. 297-307, v.18.

Tsukagoshi et al., "Specific Complexation with Mono- and Disaccharides That Can Be Detected By Circular Dichroism," J. Org. Chem., 1991, pp. 4089-4091, vol. 56.

Urban et al., "Minaturized multi-enzyme biosensors integrated with pH sensors on flexible polymer carriers . . . ," Biosensors & Bioelectronics, 1992, pp. 733-739, vol. 7.

Urban et al., "Miniaturized thin-film biosensors using covalently immobilized glucose oxidase," Biosensors & Bioelectronics, 1991, pp. 555-562, vol. 6.

Velho et al., "In vivo calibration of a subcutaneous glucose sensor for determination of subcutaneous glucose kinetics," Diab. Nutr. Metab., 1988 pp. 227-233, v.3.

Yokoyama et al., "Integrated Biosensor for Glucose and Galactose," Analytica Chimica Acta., 1989, pp. 137-142, vol. 218.

Nishida et al., "Development of a ferrocene-mediated needle-type glucose sensor . . . ," Medical Process Through Technology, 1995, pp. 91-103, vol. 21.

Koudelka et al., "Planar Amperometric Enzyme-Based Glucose Microelectrode," Sensors and Actuators, 1989, pp. 157-165, vol. 18.

Yamasaki et al., "Direct measurement of whole blood glucose by a needle-type sensor," Clinica Chimica Acta., 1989, pp. 93-98, vol. 93.

Sternberg et al., "Study and Development of Multilayer Needle-type Enzyme-based Glucose Microsensors," Biosensors, 1988, pp. 27-40, vol. 4.

Shaw et al., "In vitro testing of a simply constructed, highly stable glucose sensor suitable for implantation . . . ," Biosensors & Bioelectronics, 1991, pp. 401-406, vol. 6.

Poitout et al., "A glucose monitoring system for on line estimation in man of blood glucose concentration using a miniaturized . . . ," Diabetologia, 1993, pp. 658-663, vol. 36.

Hashigushi et al., "Development of a Miniaturized Glucose Monitoring System by Combining a Needle-Type Glucose Sensor . . . ," Diabetes Care, 1994, pp. 387-389, v.17, n.5.

Jobst et al., "Thin-Film Microbiosensors for Glucose-Lactate Monitoring," Anal. Chem., 1996, p. 3173-79, vol. 68.

Shults et al., "A Telemetry-Instrumentation System for Monitoring Multiple Subcutaneously Implanted Glucose Sensors," IEEE Trans. on Biomed. Eng., 1994, pp. 937-942, v41, n.10.

Wang et al., "Needle-Type Dual Microsensor for the Simultaneous Monitoring of Glucose and Insulin," Anal. Chem., 2001, pp. 844-847, vol. 73.

Moussey et al., "Performance of Subcutaneously Implanted Needle-Type Glucose Sensors Employing a Novel Trilayer Coating," Anal. Chem., 1993, 2072-77, vol. 65.

Bindra et al., "Design and In Vitro Studies of a Needle-Type Glucose Sensor for Subcutaneous Monitoring," Anal. Chem., 1991, pp. 1692-1696, vol. 63.

PCT International Search Report, Dec. 1, 2006.

* cited by examiner

INSERTION DEVICE

BACKGROUND OF THE INVENTION

1. Field of Invention

Embodiments of the present invention relate generally to an insertion device used commonly for subcutaneously puncturing a site in a patient to insert a soft cannula that forms part of an infusion set for subcutaneous delivery of a fluid, drug or other infusant by means of an external infusion system. More particularly, embodiments of the invention relate to an insertion device capable of being disposed of without the risks of causing unintended harmful injuries to persons.

2. Description of Related Art

Insertion devices are generally used in the field of subcutaneous infusion sets. These infusion sets are used for delivering a fluid, medication or other infusant, for example, insulin, to a subcutaneous site in a patient. Such an infusion set is described, for example, in U.S. Pat. Nos. 6,520,938 and 6,056,718, which are herein incorporated by reference. Another example is described in co-pending U.S. application Ser. No. 11/003,225, entitled Medication Infusion Set, filed on Dec. 3, 2004, which is herein incorporated by reference. These devices commonly include a delivery tube connected to an infusion pump or other fluid or medication delivering device. Such an infusion set may include a base portion with a cannula deposited in the skin of a patient, and an adhesive patch at the base of the cannula housing to hold the cannula in place. The cannula is inserted into the skin of a patient, with the aid of an insertion device, to facilitate the subcutaneous transfer of an infusant. The possibility of disconnecting the infusion set from other parts of the infusion system is provided in order to improve the user comfort.

The use of a cannula further improves patient comfort. The cannula is generally more flexible than a rigid needle and allows the user to perform activities with much less pain or discomfort. While this allows for increased mobility, there remain disadvantages to patients for other reasons. To insert the cannula in place, an insertion device, commonly including a needle, is used and then discarded after attaching the cannula to the infusion site. Therefore, upon withdrawal of an insertion device from the base, there are potential risks of unintended harm from the sharp end to the user or others.

Because of the risk of harm during or after disposal of the insertion device, it is helpful if the insertion device can be quickly and securely covered. And because each insertion device may travel to numerous locations during the disposal process, and be handled by many different people, it is advantageous if the coverage withstands the entire process and remains secured after it reaches its final disposal location. Therefore, it would be useful to provide an insertion device with a way in which the needle can be covered quickly and securely after use and the insertion device discarded without the danger of causing unintended harmful injuries to persons.

While some insertion devices in the art provide ways to cover the exposed needle, there are disadvantages. In general, known insertion devices involve separate pieces that require the user to fit the pieces together. The cumbersome assembling process takes additional time and space. Moreover, the assembling process itself presents additional dangers of suffering needle pricks. Other known insertion devices, while not requiring assembly of separate pieces, involve complicated maneuvering to cover and secure the needle. A known insertion device is described in U.S. Pat. No. 6,355,021. The insertion device comprises a needle and hub. The hub includes a pivotable shield that can be manipulated to cover the needle as well as interlock the entire insertion device.

BRIEF SUMMARY

In accordance with an embodiment of the invention, an insertion device has been developed that can be used in connection with an external infusion system. The insertion device includes a needle at one end adapted for facilitating a subcutaneous puncture and a hub at the opposite end. The hub includes a handle part and a guard part and further includes a locking mechanism engaged by the interaction of the guard part and the handle part. The interaction of the guard part and the handle part facilitate a position wherein the rigid needle is covered by the guard part.

The insertion device may be used in conjunction with an infusion device that has a cannula. The insertion device allows quick and easy placement of the cannula of an infusion set through the skin of the user at an infusion site to provide a subcutaneous path for an infusant. An adhesive patch may be included at the base of the cannula housing to hold the placement of the cannula. After the placement of the cannula and infusion set, the insertion device is removed and the infusant may be delivered.

Embodiments of the invention may include a hub removably attachable to the base of a cannula housing of an infusion set. In an unlocked position, the hub contains a needle housing from which a needle extends through the base. The needle may be subcutaneously insertable into the infusion site for subcutaneously positioning the cannula. Embodiments of the invention include a guard part attached to the hub for covering the needle after use. The hub of the invention or the parts of the hub may be made out of a flexible material, such as polypropylene, although it may also be made out of a non-flexible material, such as polycarbonate, if preferred. Alternatively, the hub of the invention or the parts of the hub may be made out of any suitable flexible or non-flexible materials such as polyethylene, polyurethane, polyvinyl chloride, resins, polymers, ceramics, composites, or the like.

In one embodiment there is provided a hub removably attachable to the base of a cannula housing of an infusion set, including a handle part extending from one side of the hub. A guard part, in an unlocked position, is attached along the handle part and may be slid along ledges on the inside of the guard part to move in towards the needle. The guard part moves into the needle, causing the needle to bend into a needle recess formed as the guard part and the handle part are slid together. Once the guard part slides over the needle and in towards the opposite end, the locked position of the guard part with the handle part is achieved and the needle is covered. The locked position may be temporary or permanent. Finger grips comprised of textured ridges on one end of the guard part and a finger scoop positioned on the side of the handle part may be added to improve the user's grip and effectuate handling.

According to an embodiment, the hub and guard part form a needle recess in which the needle may be housed after use. This may be achieved by a guard part with a pocketed cross-section of any shape. The cross-section may include an open space in the middle, or in proximity to the middle, surrounded by the pocket walls of the handle part, except an opening on one side, forming a needle recess along the guard part for the needle to enter. The guard part that fits over the needle recess may facilitate pushing the needle so that it is directed into the needle recess. There may be a positive stop further included as a structure at one end of the hub which provides a limit on how far the guard part moves. As the guard part moves into and over the needle, the guard part continues to move along the handle part until it reaches the structure and the surface of the structure contacts part of the hub. At this point the guard part reaches the positive stop. Additional stops included as part of the guard part may also limit how far the guard part moves.

The guard part and the handle part engage a locking mechanism when the handle part and the guard part are slid with respect to one another. The locking mechanism may be engaged temporarily or permanently. The locks may include detents on either side of one end of the guard part that fit into corresponding catches on the inner sides of the handle part. The detents can fit into the catches when the guard part is pushed in towards the needle and slid along the needle recess of the handle part. In the locked position, the detents fit into the corresponding catches and hold the guard part and the handle part in a locked position in which the needle is secured inside the needle recess. As another alternative, the needle may be secured within the guard part and the hub by alternative locking structures to catches and detents, such as hooks, barbs, or other connecting pieces.

In the embodiment, other safety features may be included. For example, a needle notch can be placed inside the hub on the end wherein the needle tip is directed by the guard part. The needle notch includes a block that keeps the needle tip in place. The needle notch further ensures that there cannot be unintended contact with the needle tip.

In another embodiment of the invention, a hub removably attachable to the base of a cannula housing of an infusion set may include a handle part and a guard part, with a collapse part on one side of the hub and a guard part on the opposite side. The collapse part is attached to a push block within the hub. The collapse part is an area on the hub that can flex and collapse inwards when pressure is added. The collapse part may be composed of any suitable material that will allow it to be flexed without fracturing. The opposing walls of the collapse part are biased to improve the wall collapse when pressure is applied. This inward collapse of the walls facilitate the pressure of the collapse part on the push block. The collapse part causes the push block to flex in towards the needle housing, where the needle resides, pushing the needle so that it bends up into the guard part. The guard part may be extended to receive and cover the needle, with the guard part having a needle recess on its underside wherein the needle is received. Catches may be positioned on opposing sides of the inside of the hub to lock the needle within the guard part. When the walls collapse inward, the catches connect and hold the walls in the collapsed position. The needle, which is pushed into the needle recess, is held and secured inside the guard part in that position. The catches prevent the needle from leaving the guard part once it is pushed into the needle recess of the guard. This locked position may be temporary or permanent. As another alternative, the needle may be secured within the guard part by alternative locking structures to catches, such as hooks, barbs, or other connecting pieces. Finger grips comprised of textured ridges on the sides of the handle part may improve the user's grip and effectuate handling.

In yet another embodiment, the hub may include a handle part and a guard part slidably attached so that the guard part may be movable in relation to the handle part, with the guard part being able to slide over the needle when grasped and pulled in that direction. As the guard part is pulled over the needle, the needle can be retracted inside the guard part so that the needle is covered to avoid unintended injuries. Once the needle is within the guard, the handle part and the guard part are secured to one another by a locking mechanism. Detents on the outer sides of the handle part and catches on the inner sides of the guard part may be used to lock the handle part and the guard part. The guard part is pulled over the needle until the detents and catches correspond and interlock. In the locked position, the needle is secured within the guard part. This position may be temporary or permanent. As another alternative to this embodiment, the insertion device may have alternative locking structures to catches and detents, such as hooks, barbs, or other connecting pieces. The hub may be conveniently configured as a single piece so the transition to cover the needle comprises one sliding motion within one piece. To effectuate the handling of the insertion device, the guard part may be used along with the handle part to facilitate the covering of the needle.

These features provide a simple construction that reliably functions to prevent the risk or danger of unintended injuries after the use and disposal of the insertion device in an efficient and uncomplicated manner. Some embodiments may be conveniently configured so that the insertion device is a single piece, with the guard part and the handle part movably attached together, but not separable. The configuration may help avoid the complications of assembling multiple pieces.

BRIEF DESCRIPTION OF THE DRAWINGS

A detailed description of embodiments of the invention will be made with reference to the accompanying drawings, wherein like numerals designate corresponding parts in the figures.

DETAILED DESCRIPTION

In the following description, reference is made to the accompanying drawings which form a part hereof and which illustrate several embodiments of the present invention. It is understood that other embodiments may be utilized and structural and operational changes may be made without departure from the scope of the present invention.

Figure 1:
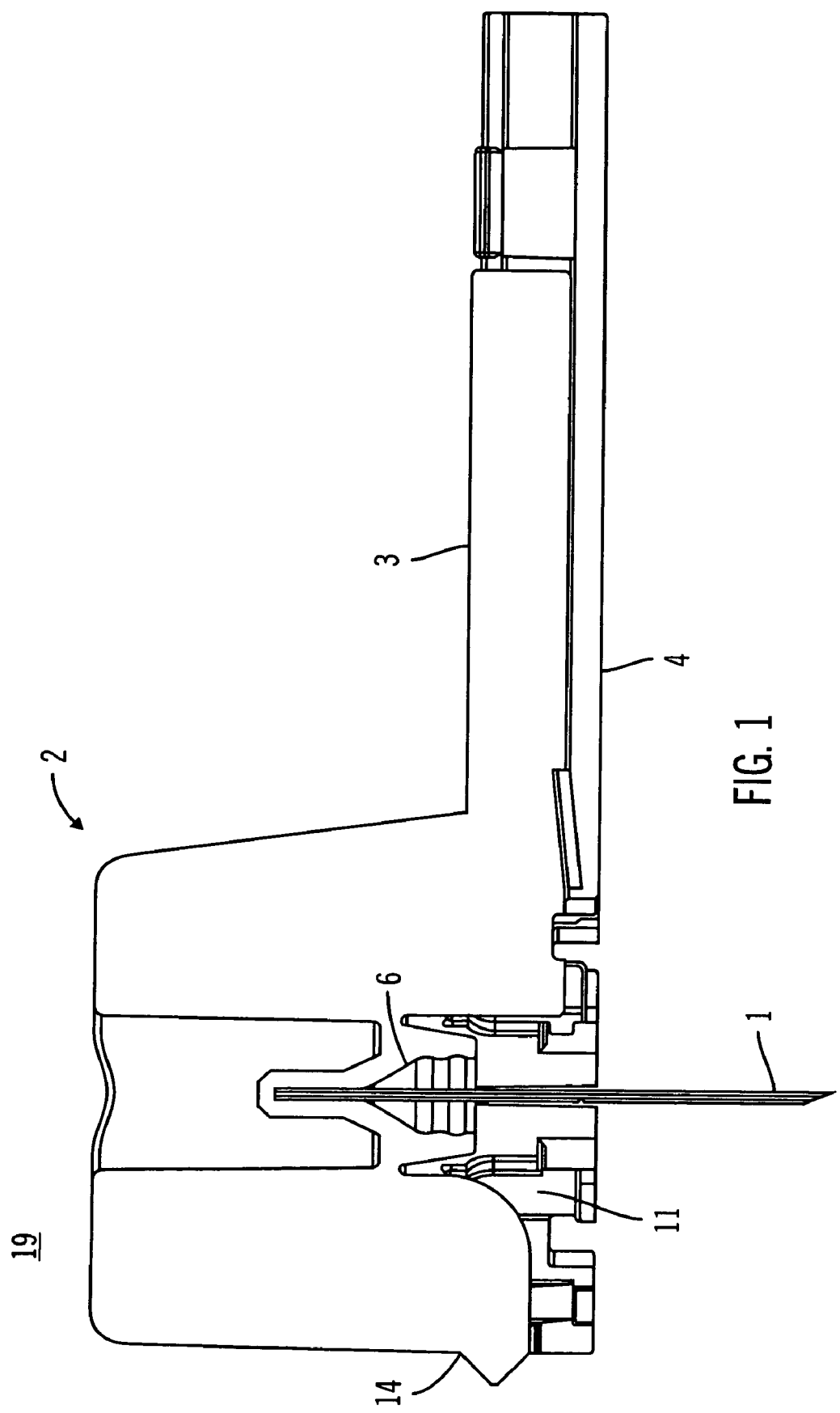
FIG. 1 is a vertical cross-sectional view of an insertion device in an unlocked position according to an embodiment of the invention.
Figure 3:
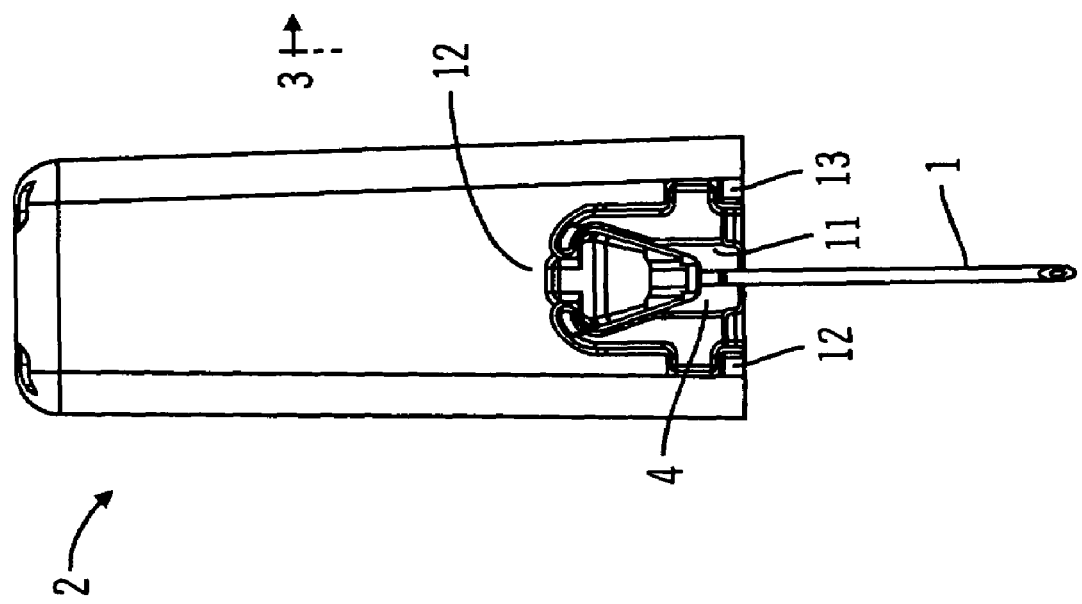
FIG. 3 is a front end view of an insertion device according to an embodiment of the invention.
Figure 5:
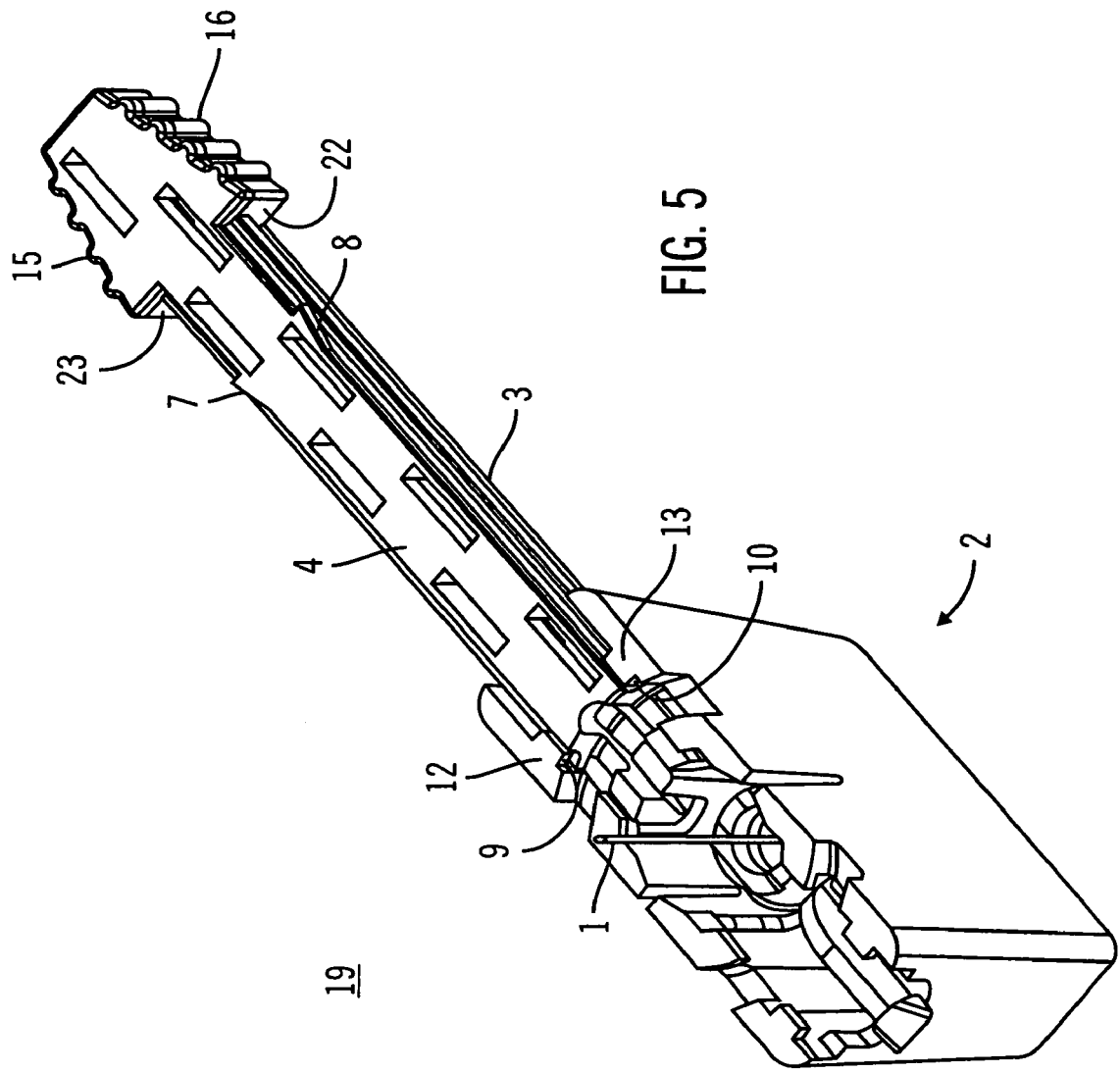
FIG. 5 is a perspective view showing the bottom of an insertion device according to an embodiment of the invention.
Figure 6:
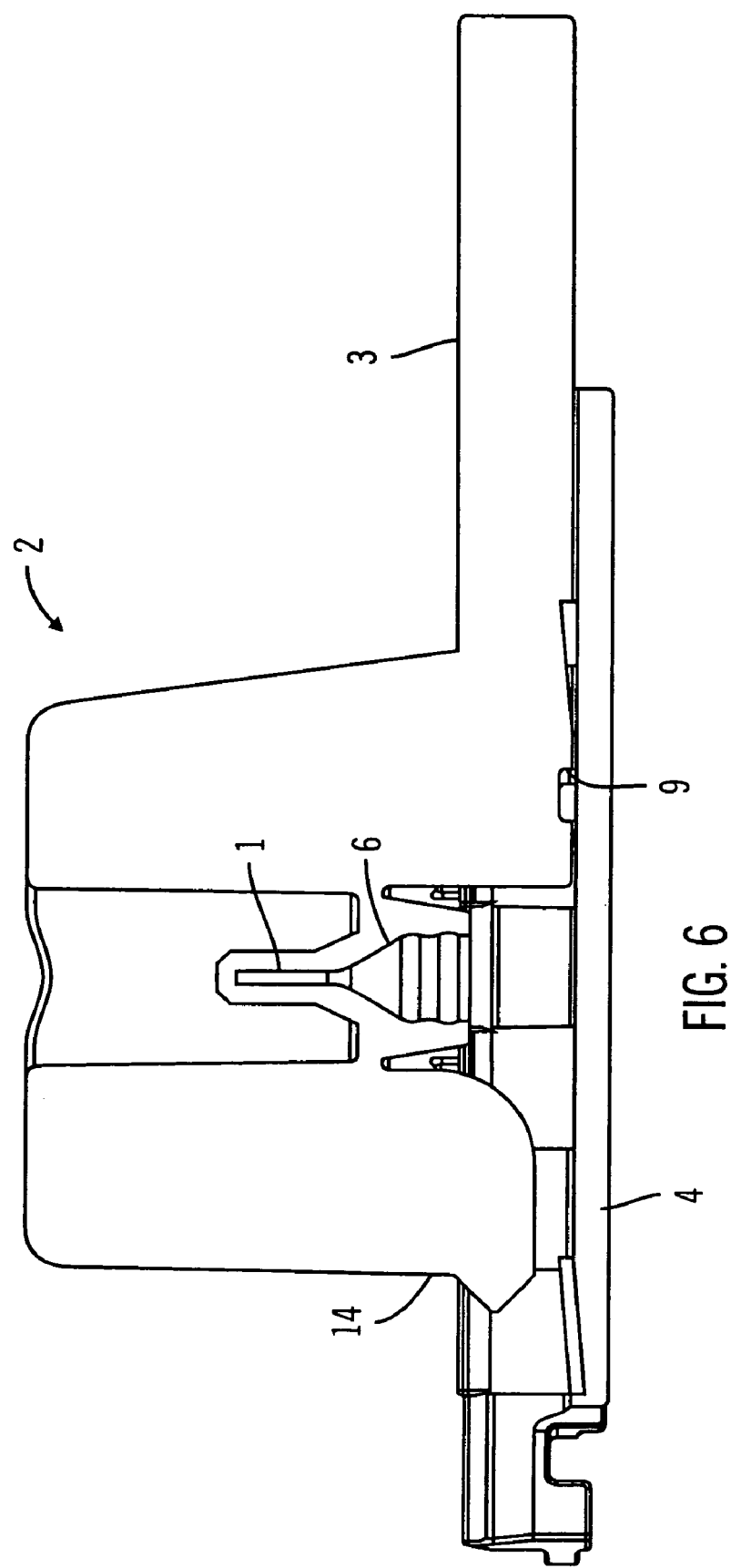
FIG. 6 is a vertical cross-sectional view of an insertion device where the guard part is slid to a locked position, according to an embodiment of the invention.
Figure 7:
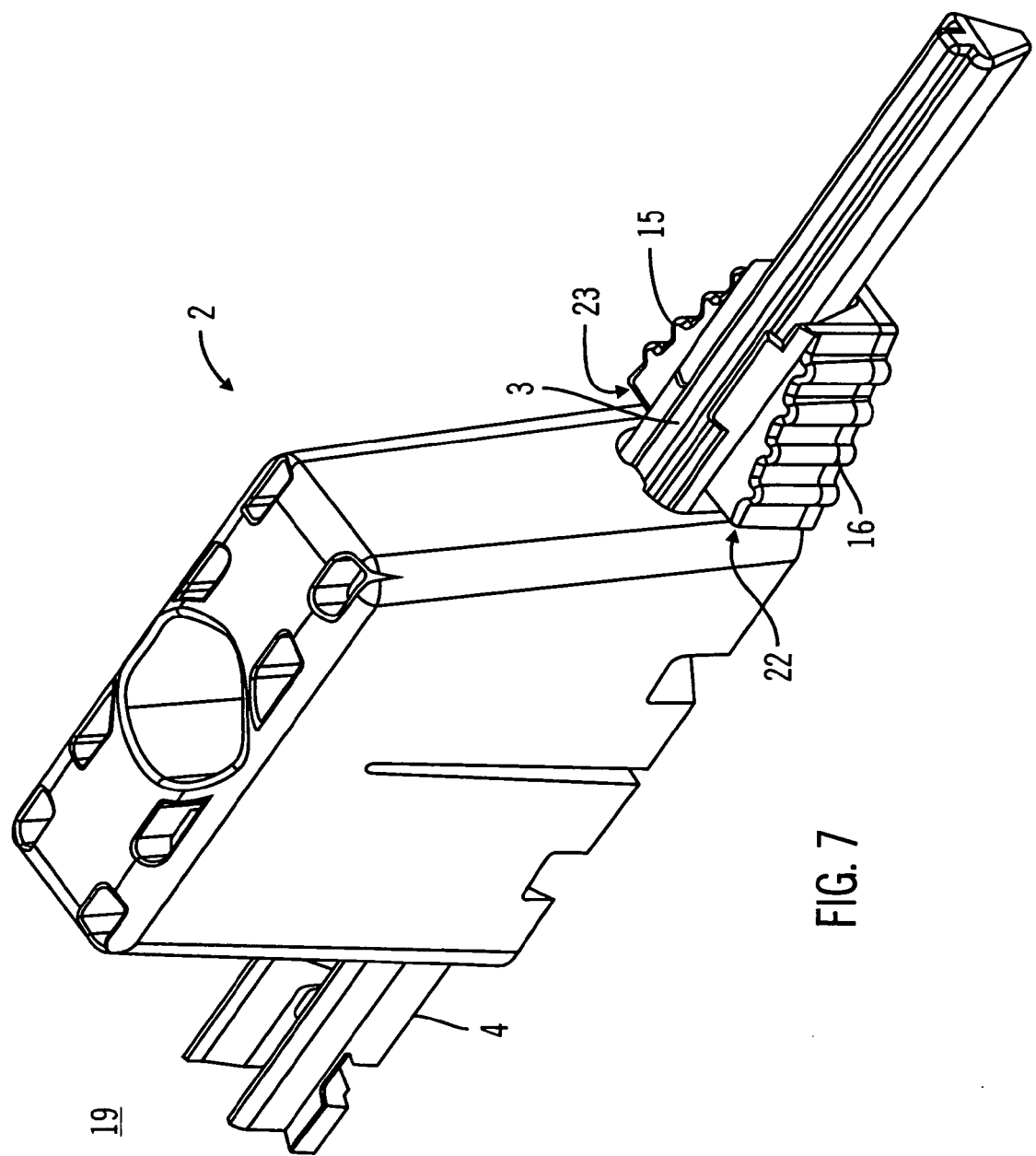
FIG. 7 is a perspective view showing the external view of an insertion device according to an embodiment of the invention.
Figure 8:
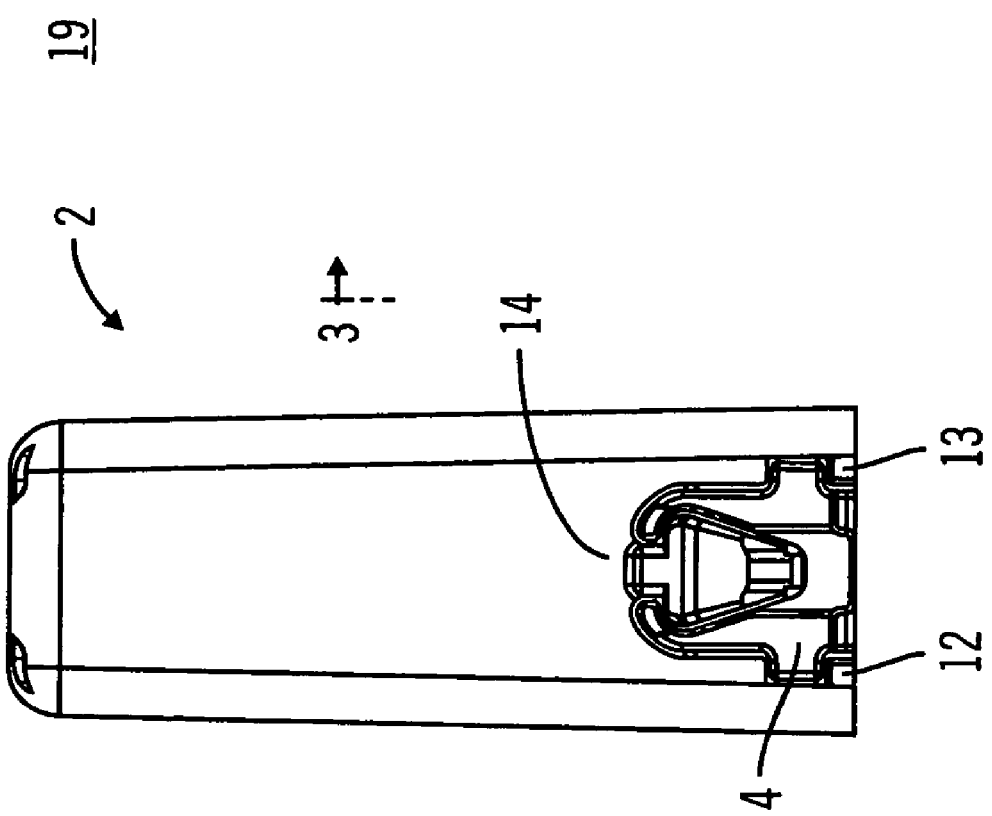
FIG. 8 is a front end view of an insertion device in the locked position according to an embodiment of the invention.
Figure 9:
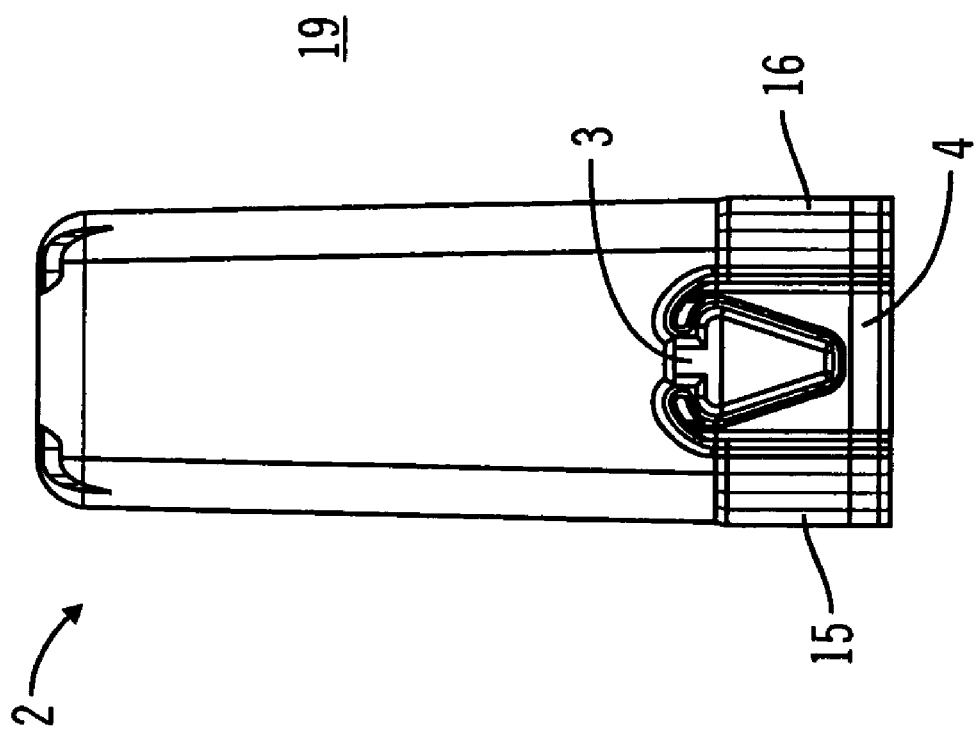
FIG. 9 is a rear end view of an insertion device in the locked position according to an embodiment of the invention.

In FIG. 1, the insertion device shown schematically by the reference numeral 19 includes a hub 2 having thereon an insertion needle 1. The needle 1 is held in place by a needle housing 6 within the hub 2. The needle 1 on the end opposite to the hub 2 is pointed or as otherwise to facilitate puncturing. The hub 2 includes a guard part 4 and a handle part 3. Along the outer end of the handle part 3, the guard part 4 is capable of slidably moving along the handle part 3. In one alternative, the handle part 3 protrudes from the hub 2 and is tubular in shape. The handle part 3 may include a pocketed cross-section that forms a needle recess (not shown). In FIG. 3 and FIG. 5, the handle part 3 further includes ledges 12 and 13 on either side of the tubular shape which hold the guard part 4 and allows it to slide laterally along the handle part 3. As shown in FIG. 5, the guard part 4 may continue to slide laterally until positive stops 22 and 23 are reached. The positive stops 22 and 23 may be created by a structure attached at one end of the guard part 4 and the hub 2 that come into contact when the guard part 4 slides far enough to cover the entire needle 1. The positive stops 22 and 23 provide a limit on how far the guard part 4 may move. Other types of stops may also be used to limit how far the guard part moves.

Figure 2:
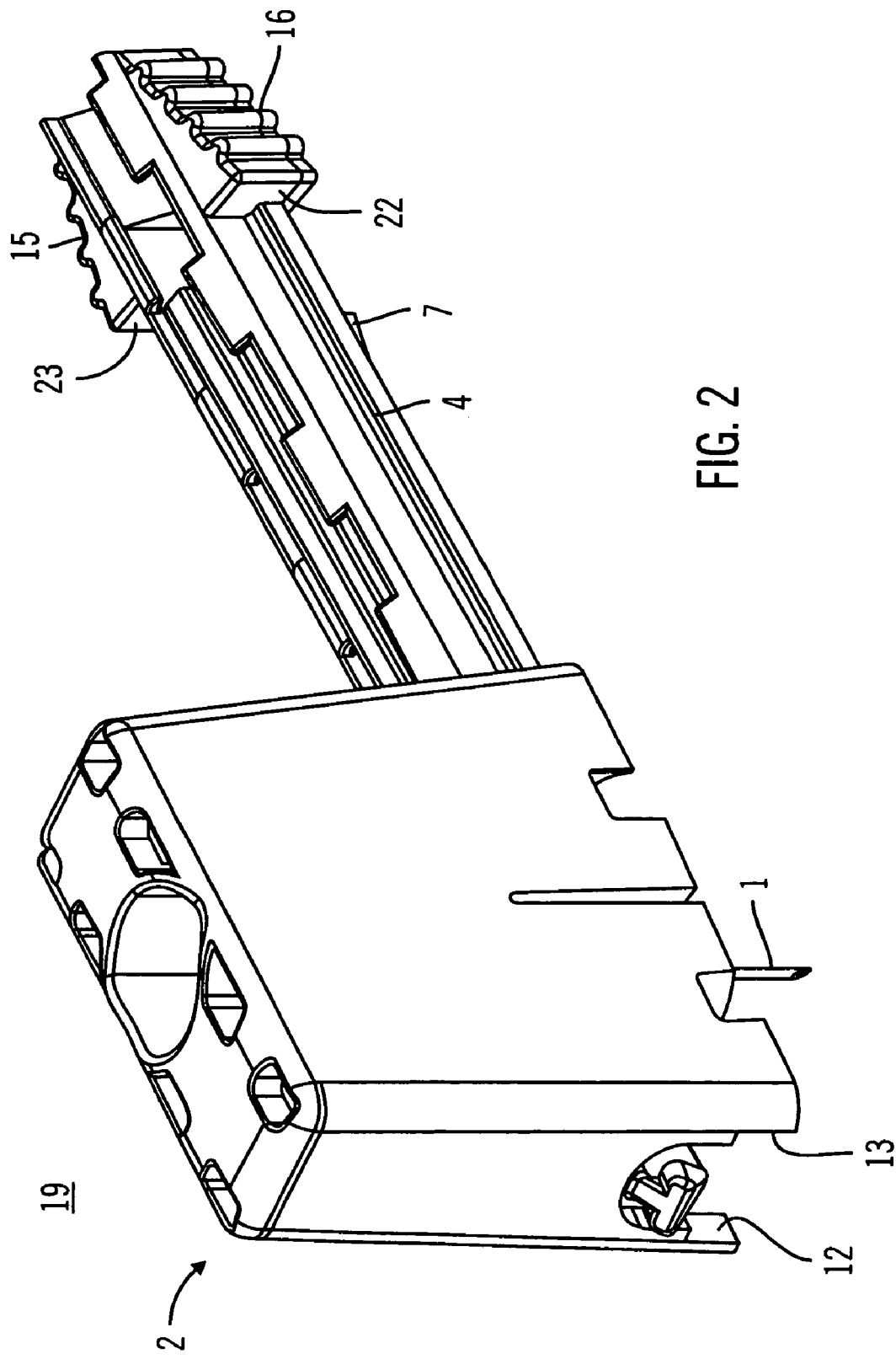
FIG. 2 is a perspective view showing an external configuration of an insertion device according to an embodiment of the invention.

In FIG. 1, the housing 6 for the needle 1 in the hub 2 is apparent. The needle housing 6 may have a circular, square or any desired cross-sectional shape. The needle 1 may be securely held in position by a press fit connection, by gluing or welding, or by being insert molded. The hub 2 of the insertion device 19 is preferably manufactured from a suitable material that flexes, such as polypropylene. However, the hub may also be made out of a non-flexible material, such as polycarbonate, if preferred. Alternatively, the hub may be made out of any suitable flexible or non-flexible materials such as polyethylene, polyurethane, polyvinyl chloride, resins, polymers, ceramics, composites, or the like. Additionally, a finger scoop 14 on the side of the handle part 3 and finger grips 15 and 16 comprising textured ridges on one end of the guard part 4 may be included to improve the user's grip and handling, as shown in FIG. 1 and FIG. 2, respectively.

Figure 13:
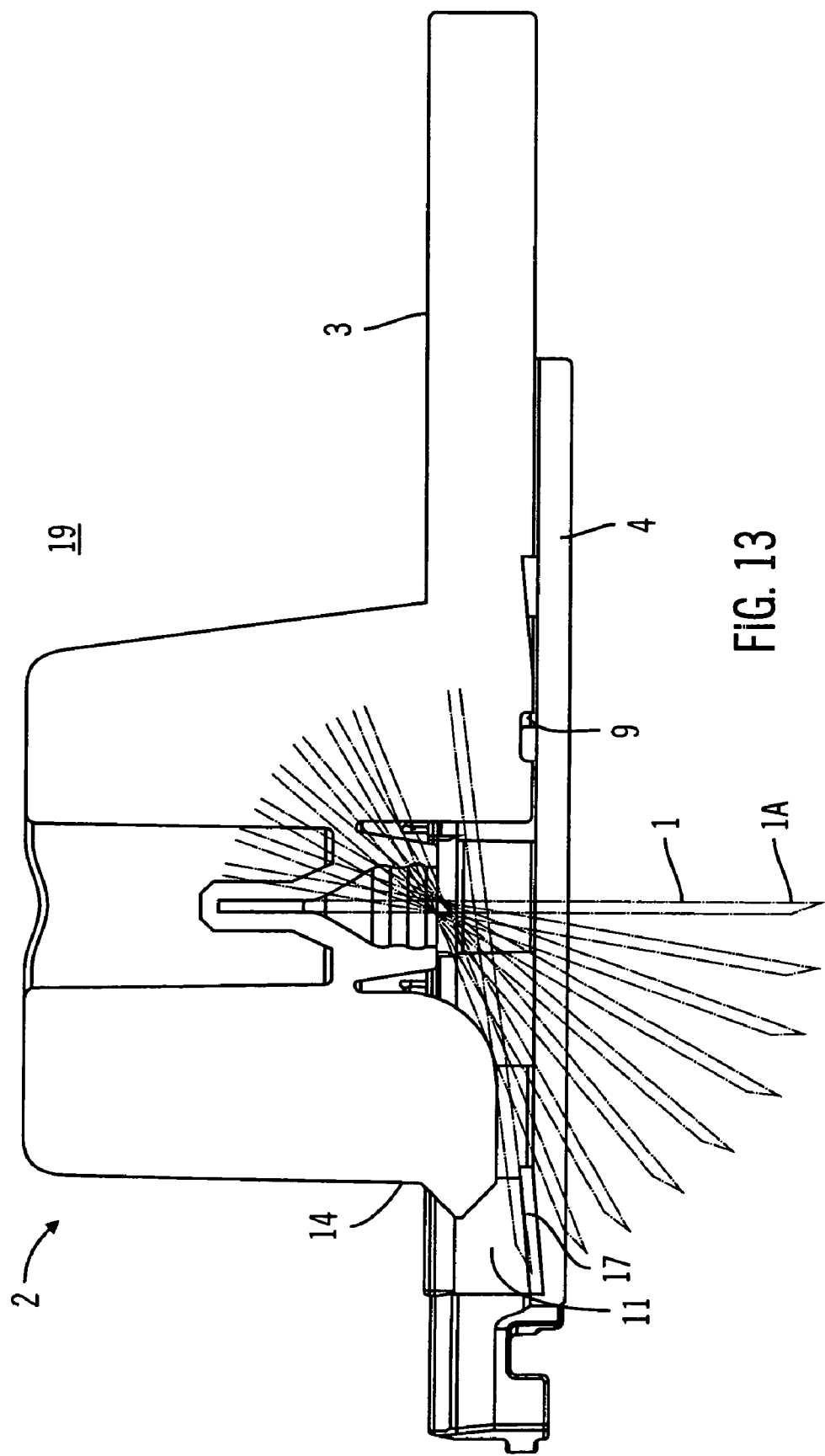
FIG. 13 is a vertical cross-sectional view of an insertion device according to an embodiment of the invention, illustrating the motion of needle when it is secured by the guard part and the handle part.

In FIG. 13, the guard part 4 may be slid along the ledges (not shown) of the handle part 3 in towards the needle 1, causing the needle 1 to be bent and pushed into the needle recess 11 formed between the handle part 3 and the guard part 4. Once the guard part 4 slides over the needle 1 and in towards the needle 1, as shown in FIGS. 6-10, the locked position of the handle part 3 and the guard part 4 is engaged where the needle 1 is covered. The locked position may be temporary or permanent. Additional safety features may be included. Shown in FIG. 13, a needle notch 17 may be located inside the guard 4 where the needle tip 1A is directed when the needle 1 is bent into the needle recess 11. The needle notch 17 may comprise a block that keeps the needle tip 1A in place. The needle notch 17 stabilizes and further secures the needle tip 1A.

In the unlocked position, as shown in FIGS. 1-5, the guard part 4 is in the unlocked position at the end of the handle part 3 away from the needle housing 6. The needle 1 is not covered and the locking mechanism is not engaged. In this unlocked position, the insertion device 19 may be used to puncture the skin of a patient.

Figure 10:
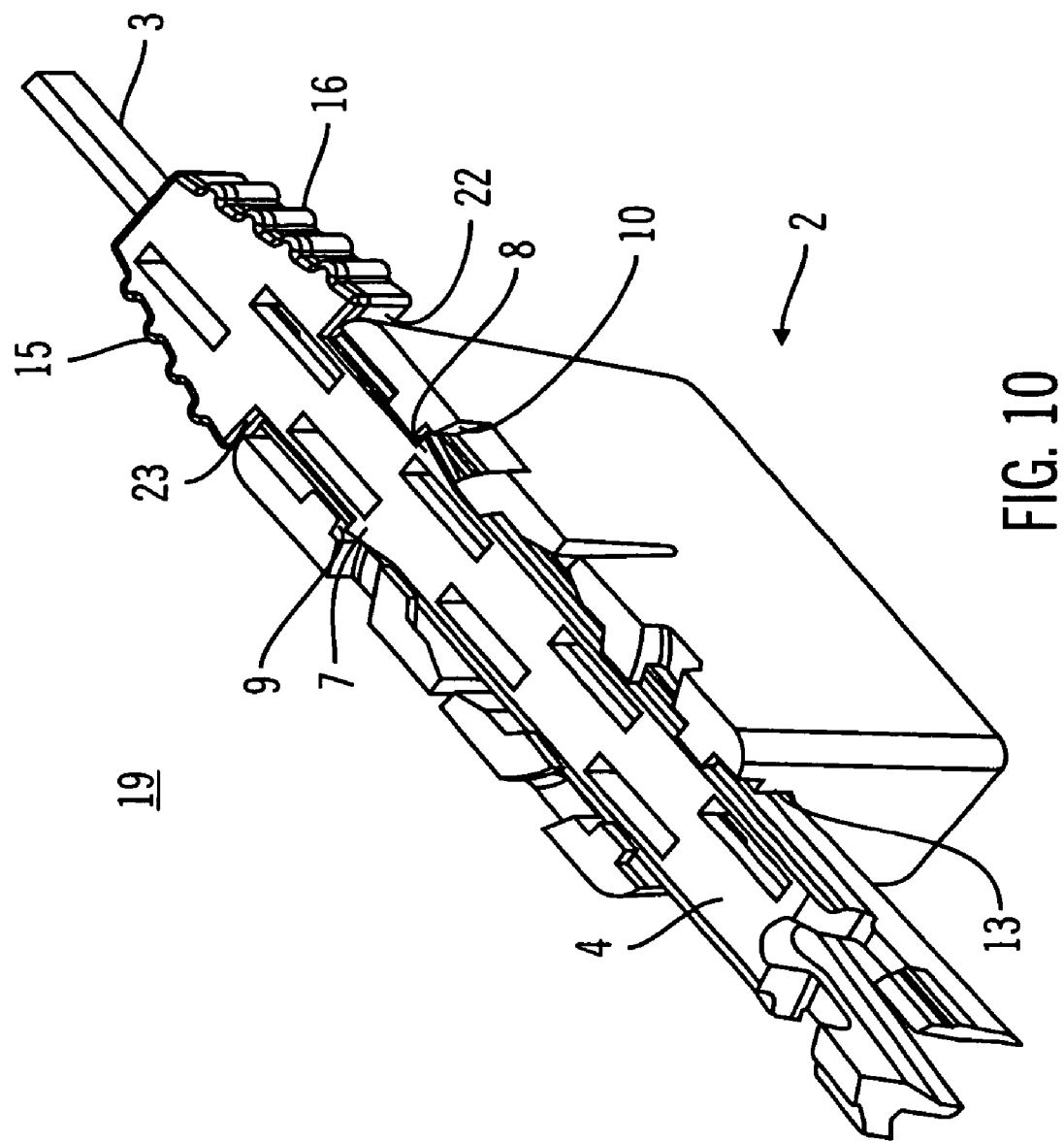
FIG. 10 is a perspective view showing the bottom of an insertion device in the locked position according to an embodiment of the invention.

In FIG. 10, the locks are detents 7 and 8 and catches 9 and 10 which are engaged once the handle part 3 and the guard part 4 are slid together as far as the positive stops 22 and 23 to secure the handle part 3 and the guard part 4 in that position. Detents 7 and 8 on either side of one end of the guard part 4 will fit into corresponding catches 9 and 10 on the inside of the handle part 3, when the guard part 4 slides along the needle recess 11 formed with the handle part 3, as the guard part 4 slides towards the needle 1 to secure the guard part 4 and the handle part 3 together. In the locked position, as shown in Fig. 10, the detents 7 and 8 will catch into the corresponding catches 9 and 10 and be held in the locked position. The needle 1. will be secured inside the needle recess 11. In other alternatives, the number of detents and catches may be varied. For example, one alternative locking structure may have one detent with one catch to connect. Additionally, an embodiment may use alternative locking structures to catches and detents, such as hooks, clips, or other connecting pieces.

Figure 4:
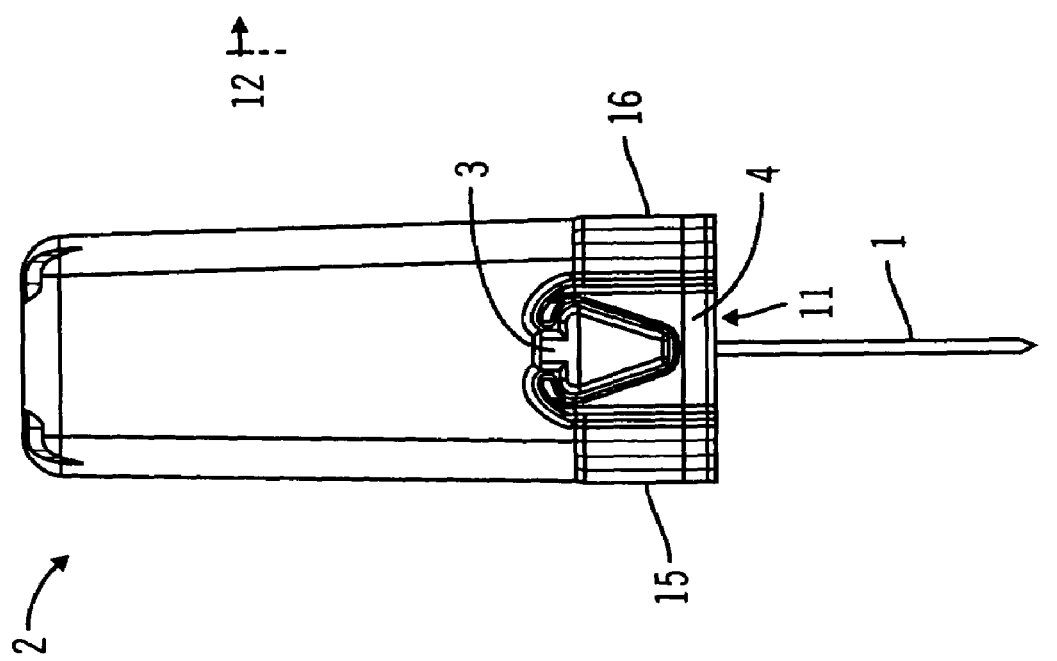
FIG. 4 is a rear end view of an insertion device according to an embodiment of the invention.

In FIG. 3 and FIG. 4, which are the front and rear views, respectively, the needle recess 11 of the handle part 3 and its interaction with the guard part 4 appears more clearly. The configuration of the needle recess 11 includes an open space in the middle surrounded by the handle part 3, except an opening on one side. The needle recess 11 is formed along the handle part 3 for the needle 1 to enter. The guard part 4 is adapted to slide along the ledges 12 and 13 of the handle part 3 to form the needle recess 11 with the handle part 3. The ledges 12 and 13 on either side of the handle part 3 interact with the guard part 4 to facilitate the sliding motion towards the needle housing 6 needed to reach the locked position. The locked position with the needle 1 secured may be disposed substantially at the end of the insertion device 19 that is opposite to the end from where the guard part 4 initially moves. In alternative embodiments, the number of ledges may be varied. For example, in one alternative insertion device, the handle part may have one inner ledge on which the guard part slides.

Figure 11:
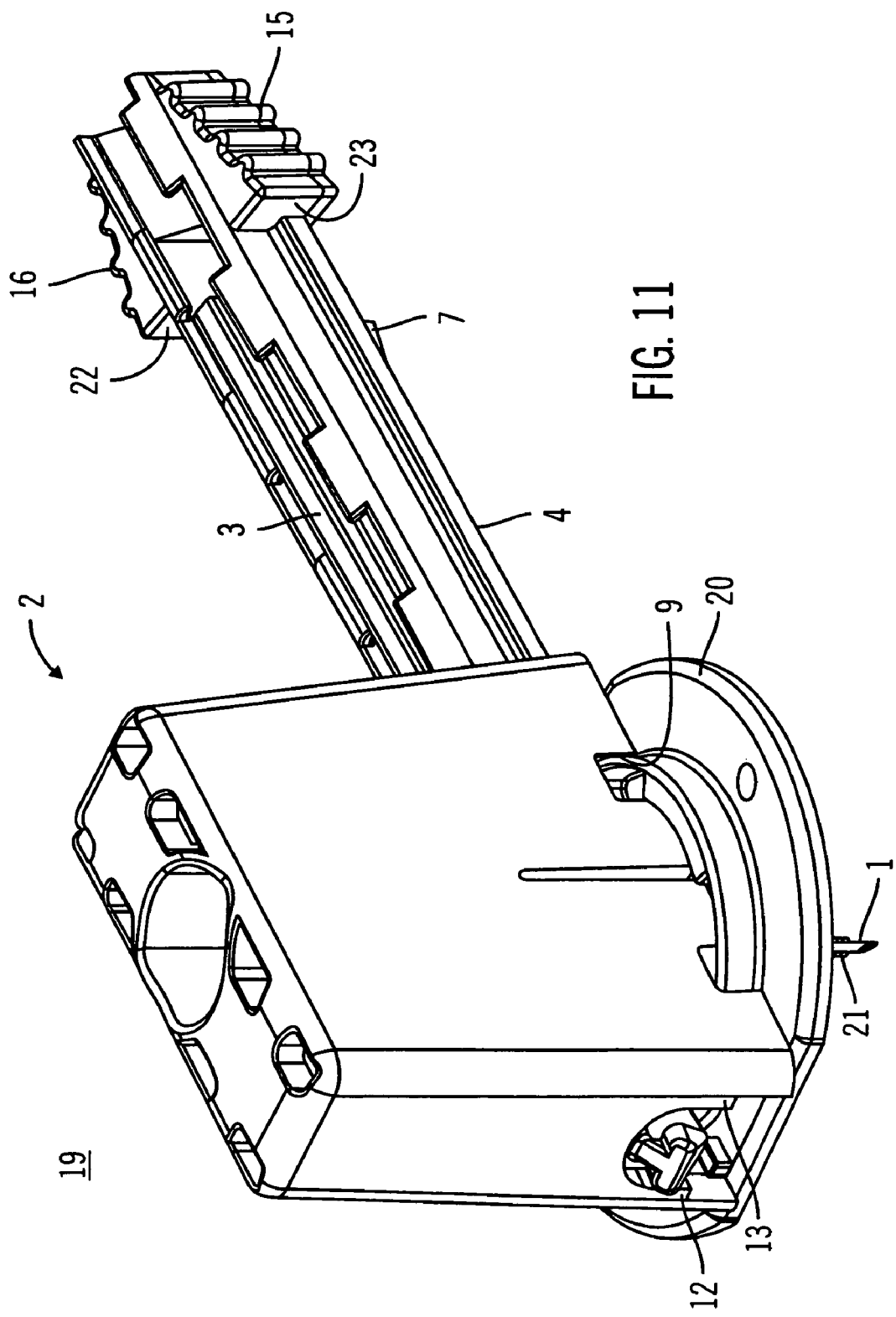
FIG. 11 is a perspective view where an insertion device is mounted on an infusion device, according to an embodiment of the invention.
Figure 12:
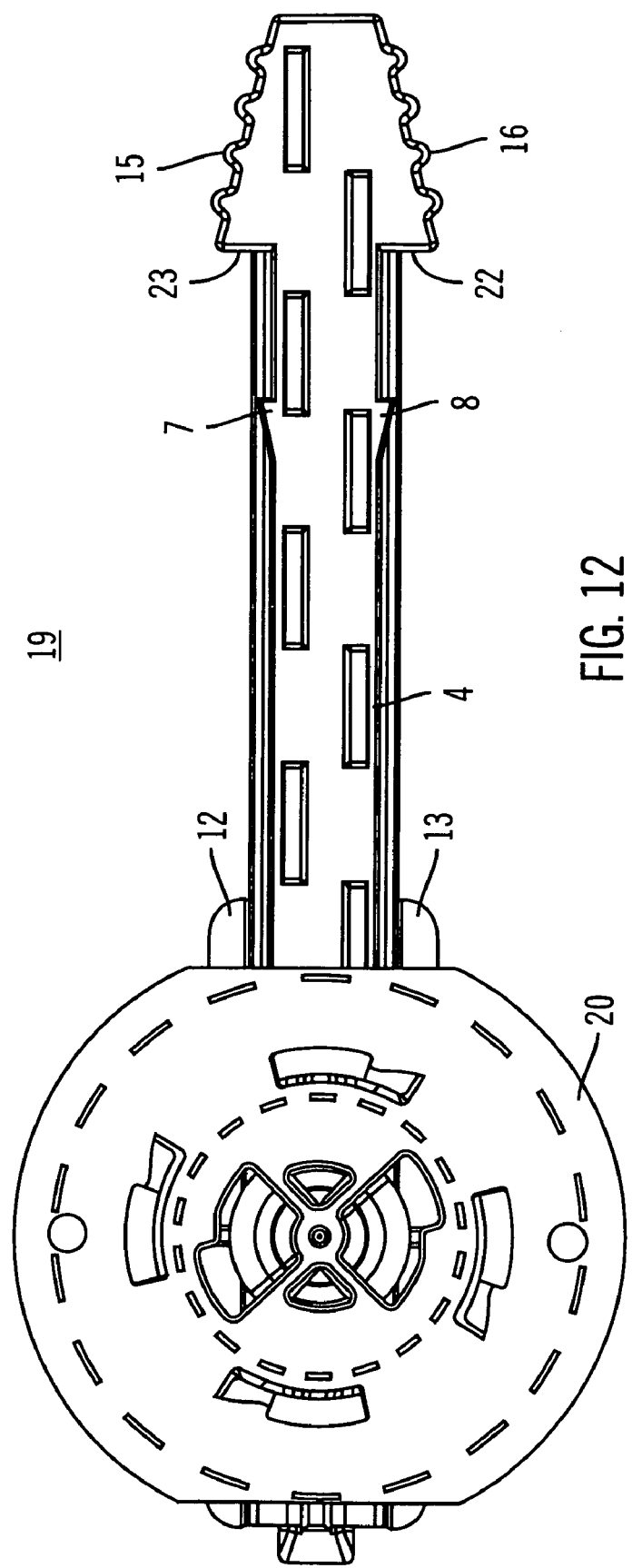
FIG. 12 is a bottom view of an insertion device according to an embodiment of the invention.

In FIG. 11 and FIG. 12, a field of use for the insertion device 19 appears. The insertion device 19 is provided for quick and easy placement of a subcutaneous infusion set 20, and may then be discarded safely. The infusion set 20 with a cannula 21 extending therefrom is shown. An adhesive patch (not shown) may also be provided to hold the cannula in place once it is deposited in the skin of the patient. The other embodiments may also be used with an infusion set in this manner.

Figure 14:
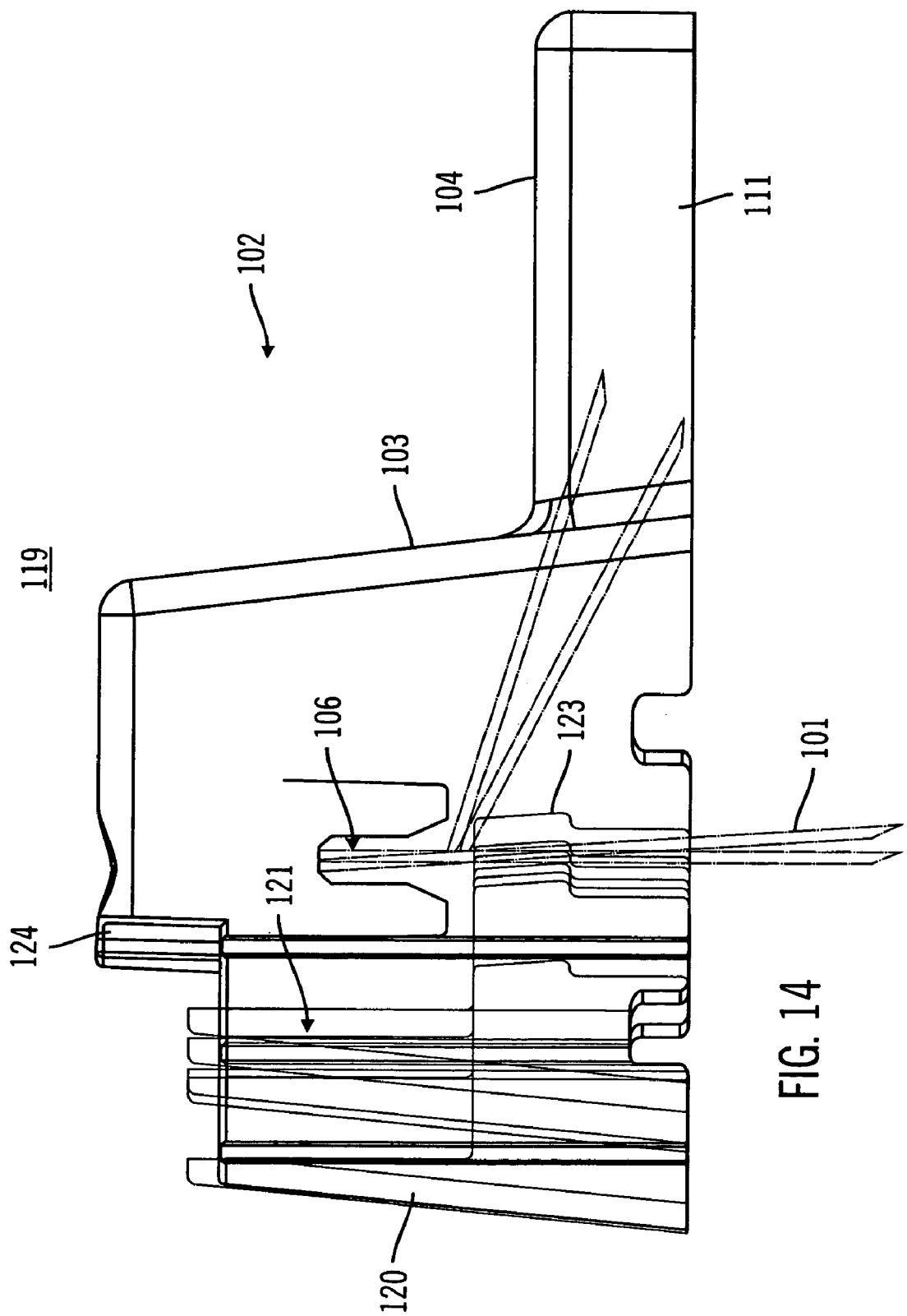
FIG. 14 is a vertical cross-sectional view of an alternative embodiment of the invention showing the manner in which the needle is brought from an unlocked to a locked position within the guard part, according to an embodiment of the invention.
Figure 23:
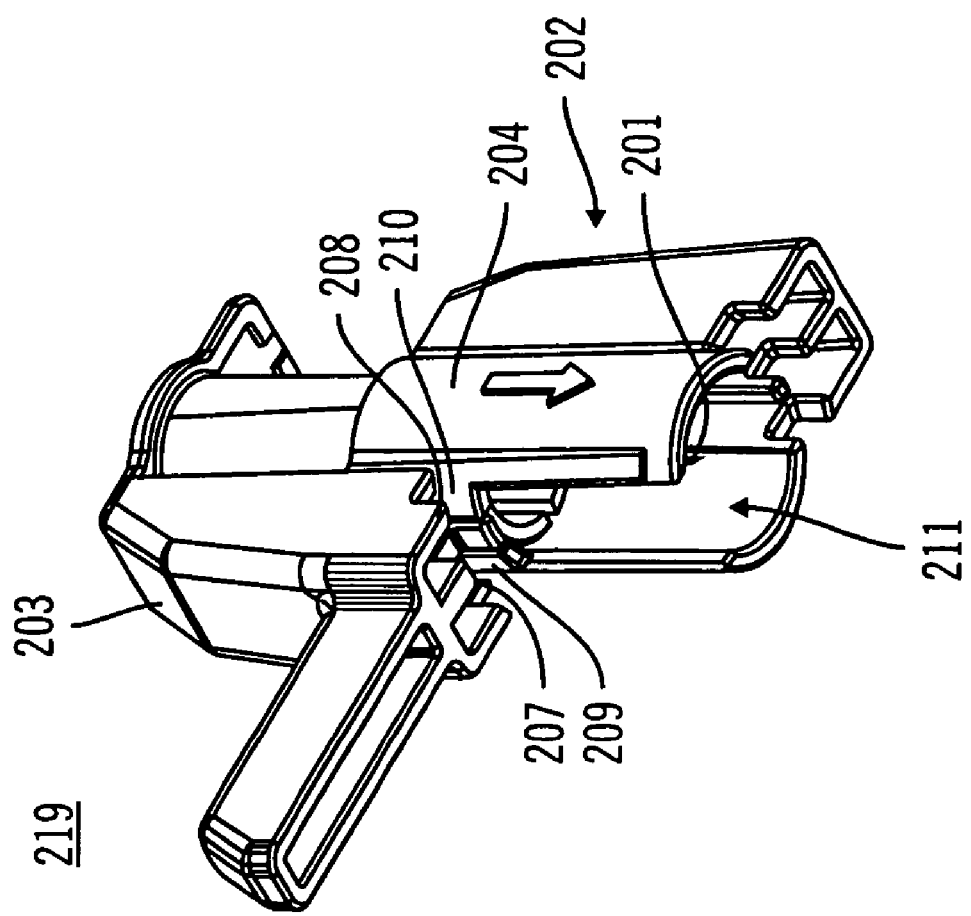
FIG. 23 is a perspective view of an insertion device according to an embodiment of the invention.

The invention provides a ready to use insertion device, which may be molded from a suitable material that is flexible, such as polypropylene. However, the device may also be made out of a non-flexible material such as polycarbonate. Alternatively, the device may be made out of any suitable flexible or non-flexible materials such as polyethylene, polyurethane, polyvinyl chloride, resins, polymers, ceramics, composites, or the like. An infusion device assembly shown in FIG. 11 and FIG. 12, as delivered from the manufacturer, including the insertion device 19 may conveniently effectuate the placement of an infusion device 20 as the assembly provides an insertion device 19 already mounted on the insertion needle 1. This may help reduce the time needed for the placement of an infusion set. Furthermore, because the insertion device 19 includes a guard part 4, it is convenient for the user to cover and secure the needle 1 prior to disposal. As best seen in FIG. 13, FIG. 14, and FIG. 23, each embodiment may be brought to locked positions prior to disposal, thereby avoiding unintended harmful injuries caused by an exposed needle.

An alternative embodiment of the invention is shown schematically in FIGS. 14-17. FIGS. 14-17 serve the purpose of explaining the principles involved in that embodiment, and the figures show schematic and cross-sectional views of the insertion device 119.

In FIG. 14, the insertion device is shown schematically by the reference numeral 119. FIG. 14 is a vertical cross-sectional view showing the manner in which the needle 101 is brought to a locked position within the guard part 104. This locked position may be temporary or permanent. In the unlocked position, the insertion device 119 may be used to puncture a site in a patient. FIG. 14 shows the insertion device 119 with a hub 102 that includes a guard part 104 and a handle part 103. The hub 102 further includes an insertion needle 101, which is held in place by a needle housing 106 within the hub 102. The needle housing 106 may have a circular, square or any desired cross-sectional shape. The needle 101 may be securely held in position by a press fit connection, by gluing or welding, or by being insert molded. The hub 102 of the insertion device 119 is preferably manufactured from a suitable material that flexes, such as polypropylene. However, the hub may also be made out of a non-flexible material, such as polycarbonate, if preferred. Alternatively, the hub may be made out of any suitable flexible or non-flexible materials such as polyethylene, polyurethane, polyvinyl chloride, resins, polymers, ceramics, composites, or the like. The needle 101 on the end opposite to the hub 102 is pointed or as otherwise to facilitate puncturing.

In FIG. 14, a collapse part 120 is shown on one side of the hub 102. The hub 102 includes a handle part 103 and a guard part 104, with the collapse part 120 attached to a push block 123 inside the hub 102. The collapse part 120 may be made of a plastics material that allows flexibility, so that pressure applied to the collapse part 120 causes it to be flexed, moving the push block 123 in towards the needle housing 106 in which the needle resides. The guard part 104 may include a needle recess 111 on its underside wherein the needle 101 is received and secured in place by catches (not shown). The guard part 104 may be extended to receive and cover the needle 101.

Figure 17:
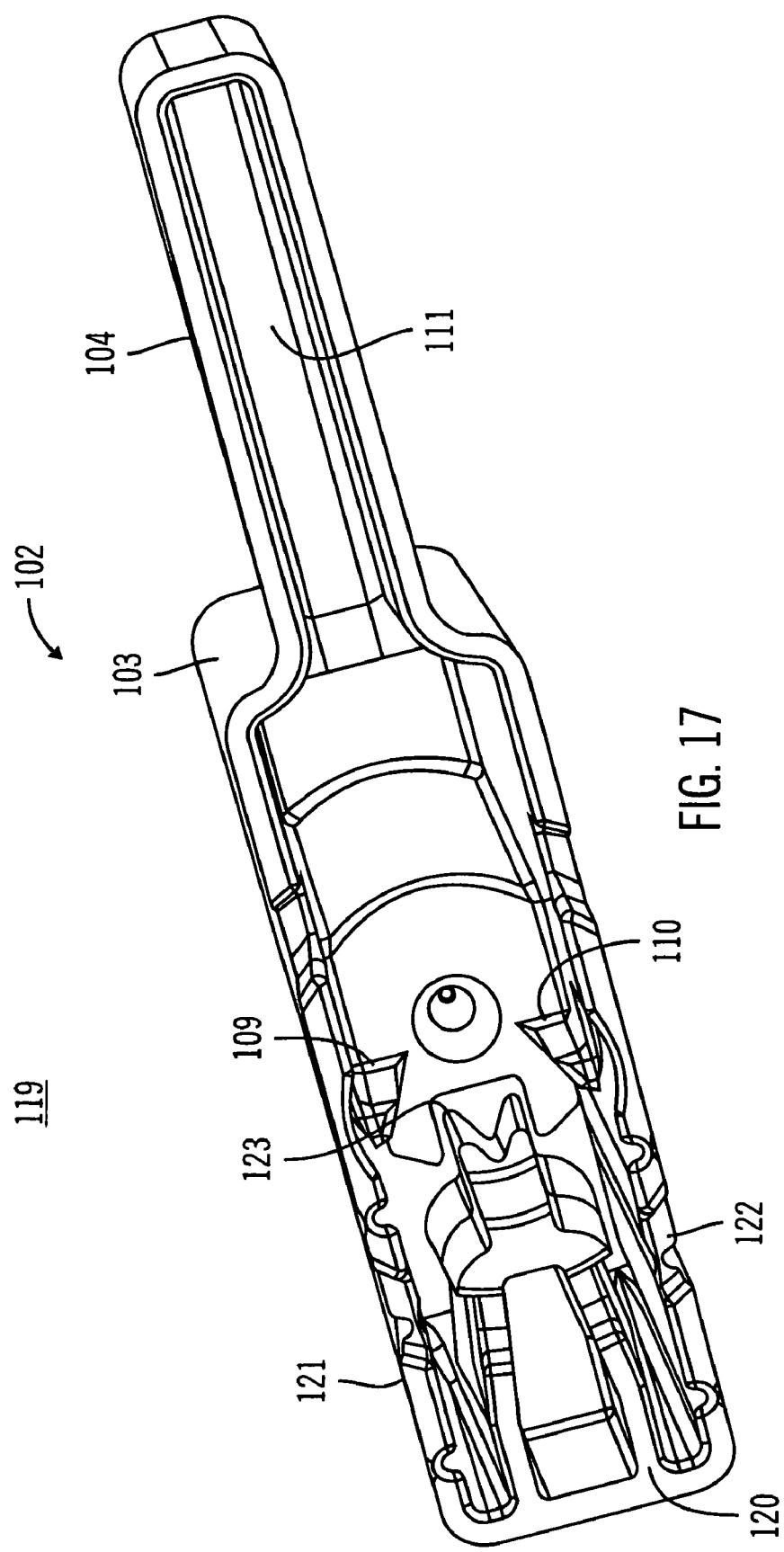
FIG. 17 is a perspective view showing the bottom of an insertion device according to an embodiment of the invention.

In FIG. 17, the catches 109 and 110 are seen to be positioned on opposing sides of the inside of the hub 102 to lock the needle (not shown) within the guard part 104. When the walls 121 and 122 collapse inward, the catches 109 and 110 connect and hold the walls 121 and 122 in the collapsed position. The needle 101, which is pushed into the needle recess 111, is held and secured inside the guard part 104 in that position. The catches 109 and 110 hold the walls 121 and 122 in the collapsed position to prevent the needle 101 from leaving the guard part 104 once it is pushed into the needle recess 111 of the guard 104. To effectuate the handling of the insertion device 119, the guard part 104 may comprise finger grips on the handle part 103 to facilitate the covering of the needle (not shown).

Figure 15:
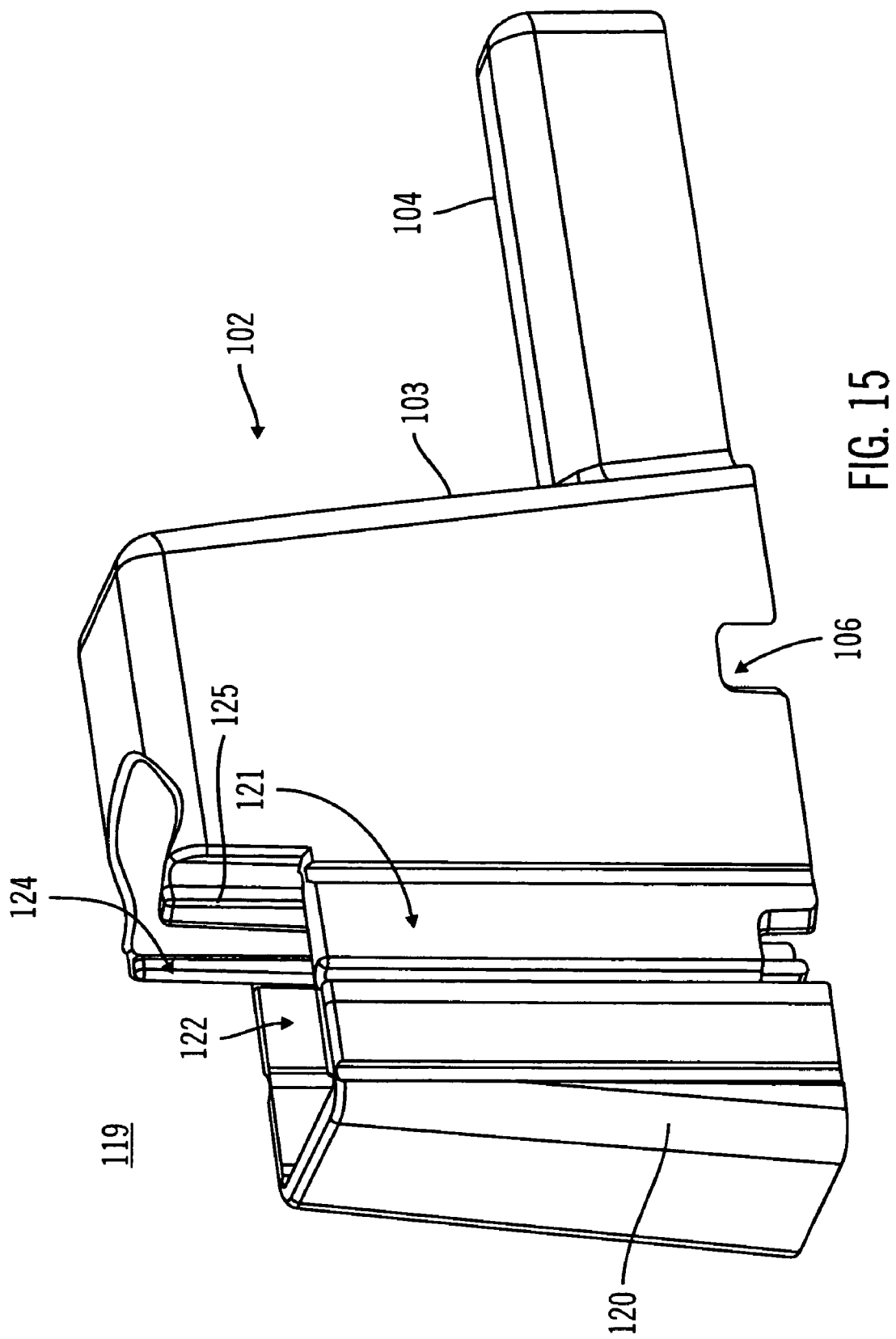
FIG. 15 is a perspective view of an insertion device according to an embodiment of the invention.
Figure 18:
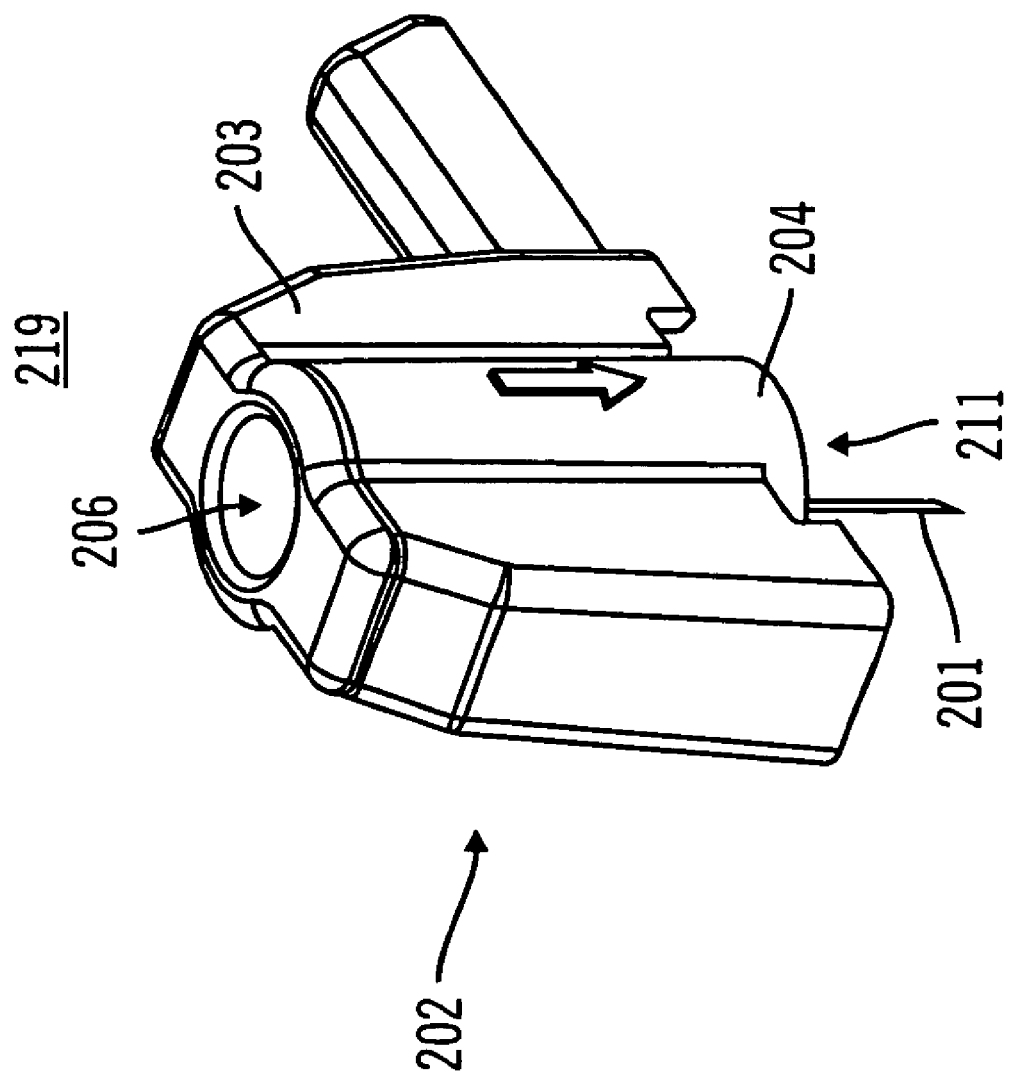
FIG. 18 is a perspective view of an alternative embodiment of the invention in an unlocked position.

In FIG. 15 the external configuration of the insertion device 119 in the locked position can be seen more clearly. The collapse part 120 includes walls 121 and 122 opposite to one another that collapse when pressure is applied to the collapse part. The walls further include an angling of material at the top of the collapse part to form biases 124 and 125. The biases 124 and 125 help improve the wall collapse when the pressure is applied. As shown in FIG. 18, this collapse facilitates the moving of the push block 123, which in turn, pushes the needle 101 up into the guard part 104.

Figure 16:
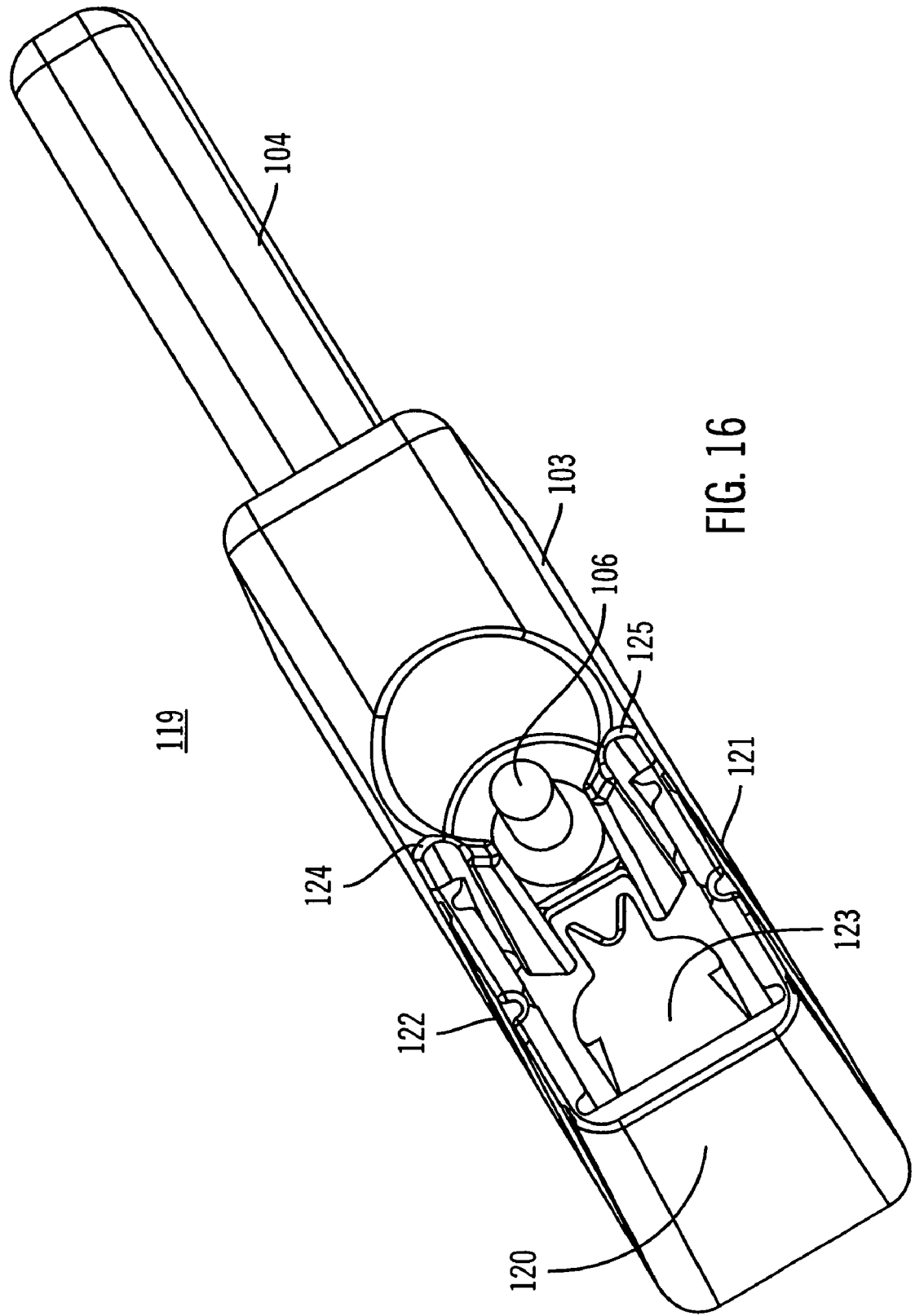
FIG. 16 is a perspective view showing the top of an insertion device according to an embodiment of the invention.

The top view of the insertion device 119 can be seen in FIG. 16. The bottom view of the insertion device 119 is illustrated in FIG. 17. The two views show the insertion device 119 in the unlocked position. The views show how the walls 121 and 122 are positioned to facilitate moving the push block 123 into the needle housing 106 so as to push the needle 101 into the guard part 104. When the needle 101 is within the guard part 104, the catches 109 and 110 secure the walls 121 and 122 in the collapsed position to lock the needle 101 inside. In other alternatives, the number of catches may be varied. For example, one alternative locking structure may have more than two catches to lock. Additionally, an embodiment may use alternative locking structures to catches, such as such as hooks, clips, or other connecting pieces.

In FIGS. 18-23, a further embodiment of the invention is illustrated. FIGS. 18-23 serve the purpose of explaining the principles involved in that embodiment, and the figures show schematic and partial cross-sectional views of an insertion device 219.

Figure 19:
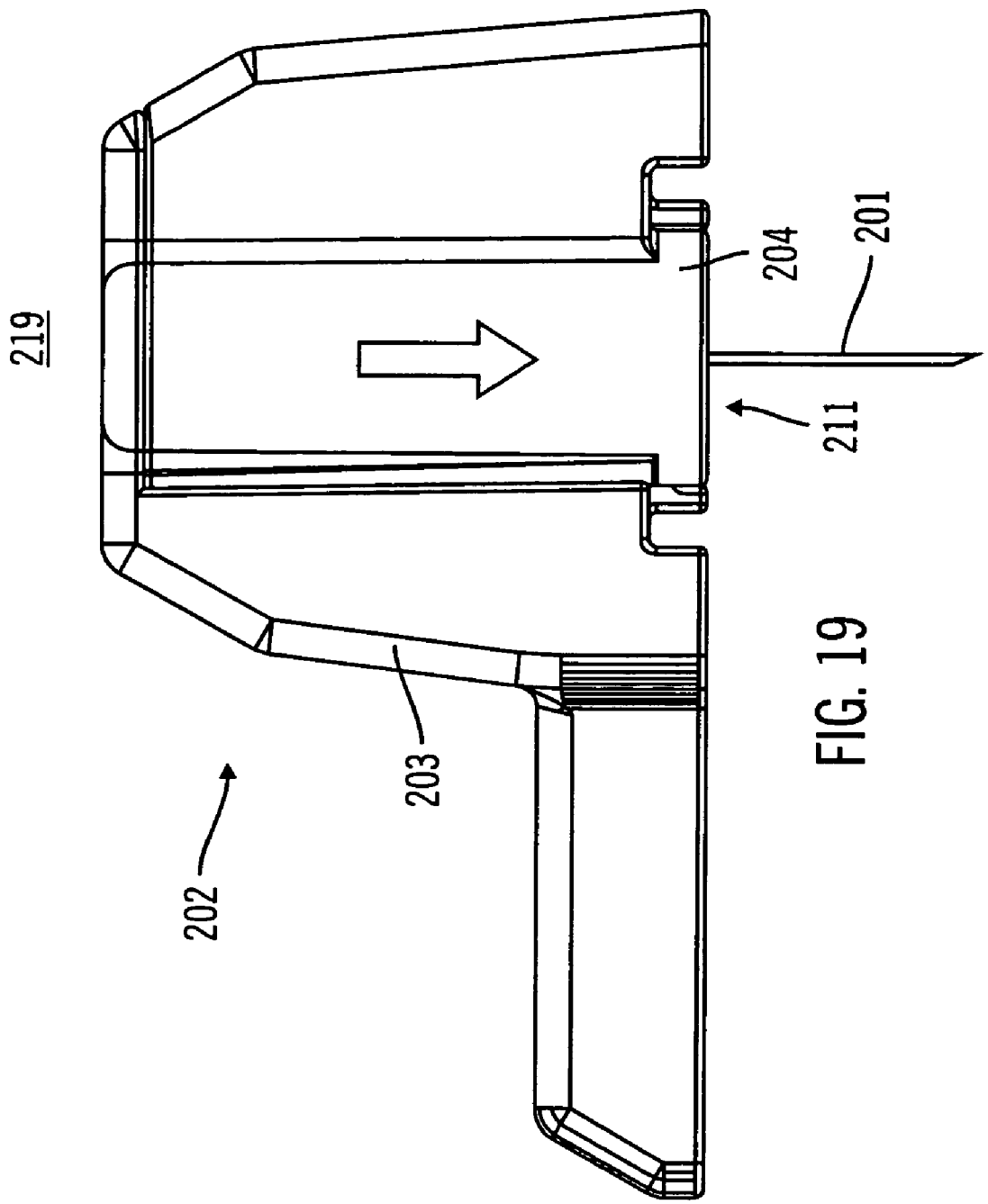
FIG. 19 is a side view of an insertion device according to an embodiment of the invention.
Figure 22:
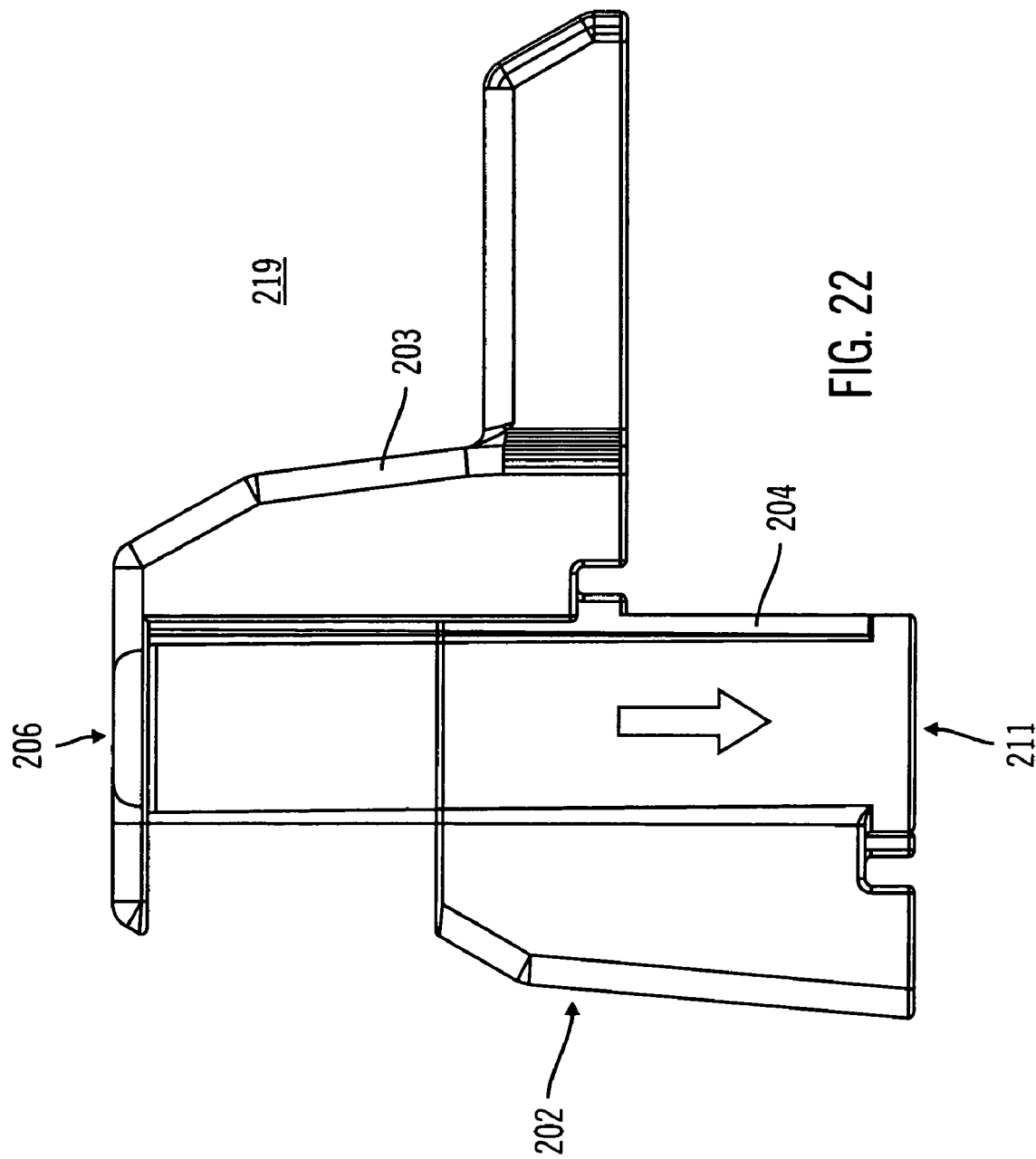
FIG. 22 is a side view showing an insertion device in the locked position, according to an embodiment of the invention.

In FIG. 18 and FIG. 19, the insertion device shown schematically by the reference numeral 219 shows a hub 202 removably attachable to the base of a cannula housing of an infusion device (not shown) that includes a guard part 204 and a handle part 203. The hub 202 further includes an insertion needle 201 to facilitate puncturing. The insertion device 219 is shown in the unlocked position. The configuration of the hub 202, including the handle part 203 and the guard part 204 connected together in one piece, is illustrated. The handle part 203 and the guard part 204 are slidably attached so that the guard part 204 may be pulled and slid along the handle part 203 over the needle 201, covering the needle 201 to avoid unintended injuries. Pulling the guard part 204 over the needle 201 allows the needle 201 to be retracted inside the guard part 204. As shown in FIG. 22 and FIG. 23, once the needle 201 is within the guard part 204, the handle part 203 and the guard part 204 are secured by a locking mechanism that may include detents 207 and 208 on the outer sides of the handle part 203 and catches 209 and 210 on the inner sides of the guard part 204. The locked position may be temporary or permanent.

In FIG. 18 and FIG. 19, the unlocked position is shown where the needle 201 is exposed and the insertion device 219 may be used to puncture. In this position the locking mechanism is not engaged. From FIG. 21, which shows the bottom view, the inside of the needle recess 211 appears more clearly. The needle 201 may be retracted into the needle recess 211 when the guard part 204 is pulled over the needle 201. When the entire needle 201 is within the guard part 204, the detents 207 and 208 and catches 209 and 210 may lock the handle part 203 to the guard part 204, securing the needle 201 inside. In other alternatives, the number of detents and catches may be varied. For example, one alternative locking structure may have one detent with one catch to connect. Additionally, an embodiment may use alternative locking structures to catches and detents, such as such as hooks, clips, or other connecting pieces.

Figure 20:
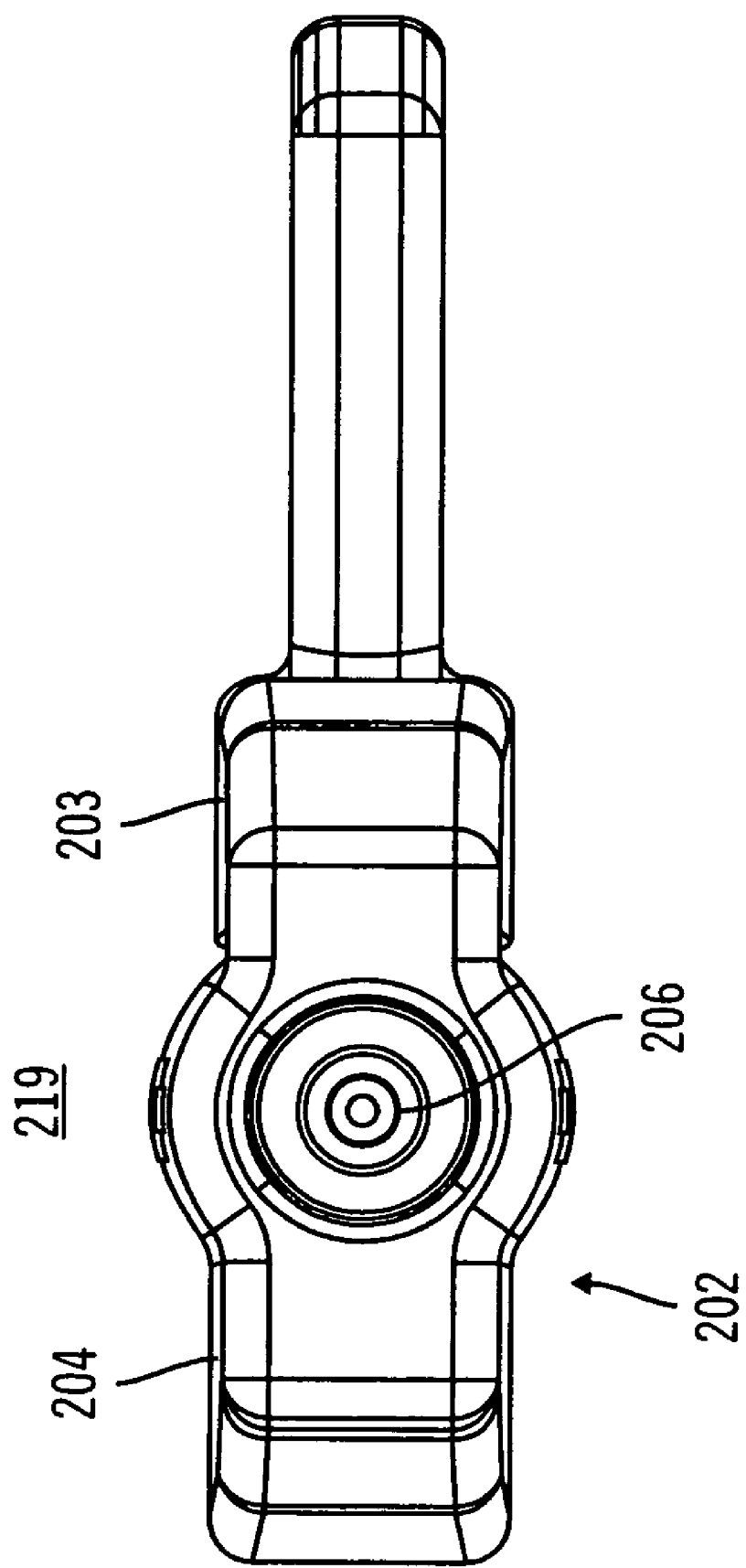
FIG. 20 is a top view of an insertion device in the unlocked position according to an embodiment of the invention.
Figure 21:
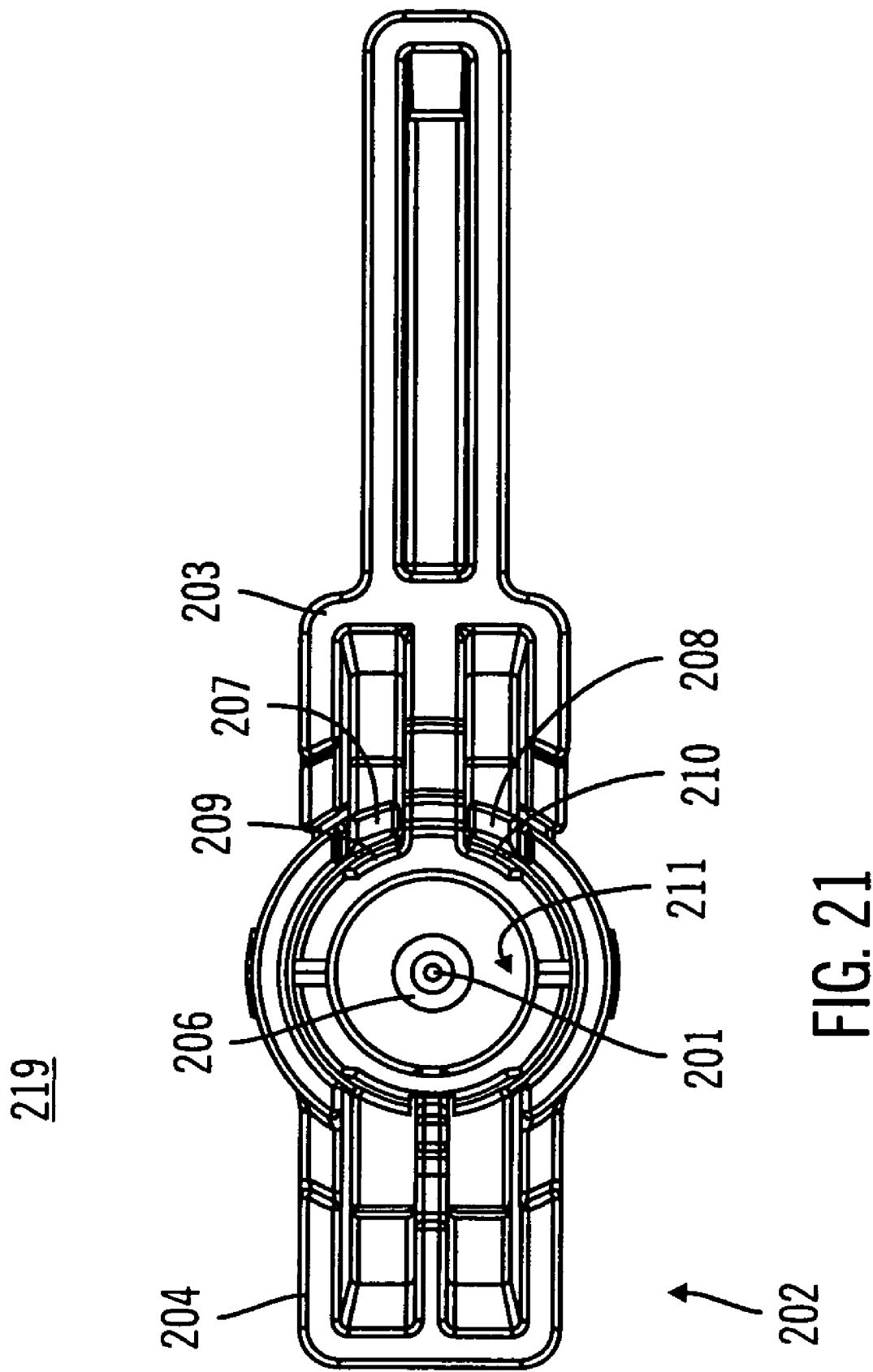
FIG. 21 is a bottom view of an insertion device according to an embodiment of the invention.

In FIG. 20 and FIG. 21, the top and bottom views, respectively, of the external side of the housing 206 for the needle 201 in the hub 202 is more apparent. The needle housing 206 may have a circular, square or any desired cross-sectional shape. The needle 201 may be securely held in position by a press fit connection, by gluing or welding, or by being insert molded. The hub 202 of the insertion device 219 is preferably manufactured from a suitable material that flexes, such as polypropylene, although a non-flexible material, such as polycarbonate, may also be used if preferred. Alternatively, the hub of the insertion device may be made out of any suitable flexible or non-flexible materials such as polyethylene, polyurethane, polyvinyl chloride, resins, polymers, ceramics, composites, or the like.

FIGS. 22-23 show the insertion device 219 in the locked position, where the needle 201 is secured within the guard part 204. The hub 202 is conveniently configured as a single piece where the transition between the handle part 203 and the guard part 204 includes one sliding motion within one piece, avoiding the assembling of separate parts when covering the needle 201. Detents 207 and 208 on the outer sides of the handle part 203 and catches 209 and 210 on the inner sides of the guard part 204 facilitate the locked position of the insertion device 219. The guard part 204 is pulled over the needle 201 until the detents 207 and 208 lock the handle part 203 and the guard part 204. To effectuate the handling of the insertion device 219, the guard part 204 may be used in conjunction with the handle part 203.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. An insertion set, comprising:
 a cannula housing of an infusion set including a cannula adapted to be inserted into the skin of a patient; and
 an insertion device including:
  a hub removably attachable to a base of the cannula housing of the infusion set, including a handle part and a guard part; and
  a needle attached to the hub, wherein the guard part is adapted to slide along the handle part to cover the needle, said handle part including a ledge on an inner side of the handle part and the guard part being adapted to slide along the ledge towards the needle and into the side of the needle wherein the needle is bent upwards.

2. The insertion set of claim 1 wherein the hub includes an inner side and a needle notch housed inside the hub where a tip of the needle is directed when bent by the guard part.

3. The insertion set of claim 1, wherein the guard part continues to slide along the ledge on the inner side of the handle part until it reaches a positive stop.

4. An insertion set, comprising:
 a cannula housing of an infusion set including a cannula adapted to be inserted into the skin of a patient; and
 an insertion device including:
  a hub removably attachable to a base of the cannula housing of the infusion set, including a handle part and a guard part; and
  a needle attached to the hub, wherein the guard part is adapted to slide along the handle part to cover the needle, wherein the guard part bends the needle into a needle recess formed as the guard part slides with respect to the handle part, and wherein the guard part and the hub cover the needle in a locked position.

5. An insertion device, comprising:
 a hub removably attachable to a base of a cannula housing of an infusion set, including a handle part and a guard part; and
 a needle attached to the hub, wherein the guard part is adapted to slide along the handle part to cover the needle, said handle part including a ledge on an inner side of the handle part and the guard part being adapted to slide along the ledge towards the needle and into the side of the needle wherein the needle is bent upwards.

6. The insertion device of claim 5, wherein the hub includes an inner side and a needle notch housed inside the hub where a tip of the needle is directed when bent by the guard part.

7. A method for covering an insertion needle, comprising:
 inserting a cannula into the skin of a patient with an insertion device, wherein the insertion device includes:
  a hub removably attachable to a base of a cannula housing of an infusion set, including a handle part and a guard part; and
  a needle attached to the hub, wherein the guard part is adapted to slide along the handle part to cover the needle, said handle part including a ledge on an inner side of the handle part and the guard part being adapted to slide along the ledge towards the needle and into the side of the needle wherein the needle is bent upwards;
 removing the insertion device from the cannula housing; and
 covering the needle of the insertion device with the guard part.

8. The method of claim 7, wherein the hub includes an inner side and a needle notch housed inside the hub where a tip of the needle is directed when bent by the guard part.

9. The method of claim 7, wherein the guard part continues to slide along the ledge on the inner side of the handle part until it reaches a positive stop.

10. A method for covering an insertion needle, comprising:
 inserting a cannula into the skin of a patient with an insertion device, wherein the insertion device includes:
  a hub removably attachable to a base of a cannula housing of an infusion set. including a handle part and a guard part; and
  a needle attached to the hub, wherein the guard part is adapted to slide along the handle part to cover the needle;
 removing the insertion device from the cannula housing; and
 covering the needle of the insertion device with the guard part, wherein the guard part bends the needle into a needle recess formed as the guard part slides with respect to the handle part, and wherein the guard part and the hub cover the needle in a locked position.

* * * * *